US011229754B2

(12) United States Patent
Eicher et al.

(10) Patent No.: US 11,229,754 B2
(45) Date of Patent: Jan. 25, 2022

(54) NEBULIZER AND RESERVOIR

(71) Applicant: Boehringer Ingelheim International GmbH, Ingelheim am Rhein (DE)

(72) Inventors: Joachim Carl Herbert Eicher, Ingelheim am Rhein (DE); Alfred Von Schuckmann, Kevelaer (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 19 days.

(21) Appl. No.: 16/630,988

(22) PCT Filed: Jul. 23, 2018

(86) PCT No.: PCT/EP2018/069927

§ 371 (c)(1),
(2) Date: Jan. 14, 2020

(87) PCT Pub. No.: WO2019/016408

PCT Pub. Date: Jan. 24, 2019

(65) Prior Publication Data

US 2020/0261666 A1 Aug. 20, 2020

(30) Foreign Application Priority Data

Jul. 21, 2017 (EP) .................................... 17020315
Jul. 20, 2018 (WO) ................. PCT/EP2018/069848

(51) Int. Cl.
*A61M 11/00* (2006.01)
*A61M 15/00* (2006.01)
(Continued)

(52) U.S. Cl.
CPC ........ *A61M 11/007* (2014.02); *A61M 15/005* (2014.02); *A61M 15/009* (2013.01);
(Continued)

(58) Field of Classification Search
CPC ........... B05B 11/00446; B05B 11/0038; B05B 11/00442; B05B 11/0008; B05B 11/3035;
(Continued)

(56) References Cited

U.S. PATENT DOCUMENTS 5,429,122 A * 7/1995 Zanen ............... A61M 15/0065 128/200.22
5,435,282 A * 7/1995 Haber ............... A61M 15/0065 128/200.14

(Continued)

FOREIGN PATENT DOCUMENTS

EP 2614848 A1 7/2013
GB 2291135 A 1/1996

(Continued)

OTHER PUBLICATIONS

International Search Report for corresponding PCT Application No. PCT/EP2018/069927, 2 pages, dated Nov. 10, 2018.

*Primary Examiner* — Vishal Pancholi
(74) *Attorney, Agent, or Firm* — Matthew B. Dernier, Esq.

(57) ABSTRACT

A nebulizer for nebulizing a fluid and a reservoir with a fluid are proposed. The reservoir includes a collapsible bag with the fluid, where the bag extends in a circumferential direction within the housing part and wherein the reservoir is manually rotated for tensioning the nebulizer.

53 Claims, 15 Drawing Sheets

(51) Int. Cl.

| | |
|---|---|
| ***B05B 11/00*** | (2006.01) |
| ***B29C 65/02*** | (2006.01) |
| ***B29C 65/00*** | (2006.01) |
| ***B65D 83/00*** | (2006.01) |
| *B29L 31/00* | (2006.01) |

(52) U.S. Cl.
CPC .... *A61M 15/0036* (2014.02); *A61M 15/0073* (2014.02); *B05B 11/0008* (2013.01); *B05B 11/0038* (2018.08); *B05B 11/00412* (2018.08); *B05B 11/00442* (2018.08); *B05B 11/00446* (2018.08); *B05B 11/3035* (2013.01); *B05B 11/3074* (2013.01); *B05B 11/3081* (2013.01); *B05B 11/3091* (2013.01); *B05B 11/3095* (2013.01); *B29C 65/02* (2013.01); *B29C 66/1122* (2013.01); *B29C 66/232* (2013.01); *B29C 66/4326* (2013.01); *B65D 83/0077* (2013.01); *A61M 2205/07* (2013.01); *A61M 2205/75* (2013.01); *A61M 2205/8281* (2013.01); *B29L 2031/7148* (2013.01)

(58) Field of Classification Search
CPC ............. B05B 11/3074; B05B 11/3081; B05B 11/3091; B05B 11/3095; A61M 11/007; A61M 15/0036; A61M 15/005; A61M 15/0073
See application file for complete search history.

(56) References Cited

U.S. PATENT DOCUMENTS

| | | | | |
|---|---|---|---|---|
| 6,557,550 | B1 * | 5/2003 | Clarke ............. | A61M 15/0065 128/203.15 |
| 2008/0001008 | A1 | 1/2008 | Thoemmes | |
| 2018/0110942 | A1 * | 4/2018 | Lastow ............ | A61M 15/0003 |
| 2018/0140785 | A1 * | 5/2018 | Lastow ............ | A61M 15/0065 |

FOREIGN PATENT DOCUMENTS

| | | | |
|---|---|---|---|
| GB | 2495576 | A | 4/2013 |
| WO | 9921601 | A1 | 5/1995 |
| WO | 9606011 | A2 | 2/1996 |
| WO | 0049988 | A2 | 8/2000 |
| WO | 2008122018 | A1 | 10/2008 |
| WO | 2009047173 | A2 | 4/2009 |
| WO | 2009115200 | A1 | 9/2009 |
| WO | 2010094305 | A1 | 8/2010 |
| WO | 2012162305 | A1 | 11/2012 |
| WO | 2015169430 | A1 | 11/2015 |
| WO | 2016180752 | A1 | 11/2016 |
| WO | 2016180753 | A1 | 11/2016 |

* cited by examiner

NEBULIZER AND RESERVOIR

CROSS REFERENCE TO RELATED APPLICATIONS

This is a national phase application of International Application No. PCT/EP2018/069927, filed Jul. 23, 2018, which claims priority to International Application No. PCT/EP2018/069848, filed on Jul. 20, 2018, and EP 17020315.2, filed Jul. 21, 2017, the entire disclosures of which are hereby incorporated by reference.

BACKGROUND

The present invention relates to a reservoir and to a nebulizer according to the disclosed embodiments and claims.

WO 2009/047173 A2 discloses a nebulizer for nebulizing a fluid. A container can be inserted into the nebulizer. The container comprises a rigid outer casing and a bag containing multiple doses of the fluid. The container or its casing is vented so that the bag can collapse when withdrawing fluid.

The container may be constructed as described in WO 96/06011 A2 or WO 00/49988 A2.

WO 2015/169430 A1 discloses a nebulizer comprising a replaceable container with a fluid to be nebulized. The container comprises an inseparable indicator device, wherein the container and the indicator device are axially moved during actuating and tensioning of the nebulizer. The indicator device controls locking of the nebulizer against further use if a predetermined number of uses has been reached or exceeded.

WO 2008/122018 A1 discloses a nasal drug delivery device with a housing having a spray port, a reservoir containing a fluid and a selectively actuable pump, wherein the fluid reservoir is located next to the pump.

GB 2 291 135 A discloses a device for dispensing a fluid, wherein the device comprises a delivery pump and a collapsible bag located next to the pump.

GB 2 495 576 A discloses a single-use fluid delivery device comprising a housing and a piston pump, wherein the piston pump comprises a container defining a pump chamber in which the fluid to be dispensed is stored prior to discharge.

SUMMARY

Object of the present invention is to provide an improved nebulizer and an improved reservoir, preferably wherein the total volume of fluid can be increased or maximized while allowing precise metering and/or a compact design and/or a simple construction.

The above object is achieved by a reservoir and/or by a nebulizer according to the disclosed embodiments.

The present invention relates to a nebulizer for nebulizing a fluid, preferably a liquid medicament, from a preferably replaceable reservoir containing the fluid in particular in a collapsible bag.

According to one aspect of the present invention, the nebulizer comprises preferably an energy store or drive for driving a fluid pump and/or for nebulization, wherein the reservoir is arranged—at least partially—around the energy store or drive and/or wherein the reservoir extends—at least partially and/or circumferentially—around the energy store or drive and/or wherein the reservoir radially encloses the energy store or drive, at least partially and/or in a U-shaped manner. This allows a very high volume of the reservoir and a very compact design of the nebulizer together with the reservoir. In particular, the ratio of volume of the reservoir to the volume of the nebulizer is increased/optimized.

According to a further aspect of the present invention, the reservoir or its tank/bag is preferably arranged at least partially around the fluid pump or its pump or pressure chamber and/or wherein the reservoir extends—at least partially and/or circumferentially—around the fluid pump or its pump or pressure chamber and/or wherein the reservoir radially encloses the fluid pump or its pump or pressure chamber, at least partially and/or in a U-shaped manner. This allows a very high volume of the reservoir and a very compact design of the nebulizer together with the reservoir and/or supports precise metering due to minimized pump pressures (underpressures) required for sucking fluid from the reservoir into the fluid pump.

According to another aspect of the present invention, the reservoir comprises preferably an—in particular at least essentially flat—tank or bag extending in an annular and/or circumferential direction and/or in a U-shape manner, preferably within a housing part of the reservoir and/or around the energy store or drive and/or around the fluid pump or its pump or pressure chamber. This allows an optimized arrangement and/or a very high volume and/or a compact/simple construction.

Preferably, the tank/bag and/or its main/circumferential extension and/or its inner side/surface, i.e. the side/surface facing towards a center and/or a main/central axis of the nebulizer, is concave and/or curved/bent and/or U-shaped and/or forms a circular arc, in particular relative to an axis which preferably corresponds to the center and/or the main/central axis of the nebulizer, reservoir, fluid pump, pump or pressure chamber and/or energy store or drive or is parallel thereto.

Preferably, the tank/bag and/or its main/circumferential extension and/or its inner side extends across an angle of more than 45° or 90°, in particular of more than 120° or 180°, with regard to the axis (which is parallel or coaxial to the center and/or the main/central axis of the nebulizer, reservoir, fluid pump, pump or pressure chamber and/or energy store or drive and/or corresponds thereto).

Particularly preferred, the angle encloses the outermost points in circumferential direction of the tank/bag around the main/central axis of the reservoir.

Preferably, the main/central axis of the nebulizer, reservoir, fluid pump, pump or pressure chamber and/or energy store or drive is the longitudinal, rotational and/or motion axis of the—preferably cylindrical and/or elongated—nebulizer, reservoir, fluid pump, pump or pressure chamber and/or energy store or drive. In particular, the main/central axis is formed or defined by the reciprocating movement and/or the main longitudinal extension of the nebulizer/reservoir and/or the main direction of the nebulization.

Mostly preferred, the main/central axis of the nebulizer, reservoir, fluid pump, pump or pressure chamber and/or energy store or drive runs alongside/beside/adjacent to the tank/bag and/or transversally to main/circumferential extension of the tank/bag.

In particular, the term "around" in context of the arrangement of the tank/bag within the reservoir or nebulizer means, that the tank/bag extends across the aforementioned angle with regard to the main/central axis and/or that the tank/bag encloses/surrounds more than 45° or 90°, in particular more than 120° or 180°, of the nebulizer, reservoir, fluid pump, pump or pressure chamber and/or energy store or drive and/or its main/central axis, in particular when being viewed from above and/or in direction of the main/central axis.

Preferably, the aforementioned definitions also apply to a tank/bag which is not steadily and/or evenly curved, e.g. in shape of a ring segment, but rather comprises edges, kinks, bends or the like and/or gaps, cavities, notches, cutouts or the like in its main/circumferential extension.

As already mentioned, the tank or bag is preferably at least essentially U-shaped. In particular, the tank or bag can be angled at least once, preferably twice, within its main extension and/or in circumferential direction of the reservoir.

According to a further aspect of the present invention, a fluid pump or an associated energy store of the nebulizer is actuated or loaded or tensioned preferably by manual rotation of the reservoir, in particular of its tank or bag containing the fluid, in particular relative to a housing of the nebulizer.

The actuation or tensioning causes preferably the withdrawal of a dose of fluid from the reservoir so that the fluid pump is loaded with the dose of fluid for the next nebulization process. This allows a very simple and compact construction and/or easy operation.

According to another aspect of the present invention, the nebulizer or a fluid pump thereof comprises preferably a reciprocating conveying element and/or a reciprocating holder for holding the reservoir, in particular for holding a connector thereof, wherein the reservoir, in particular its housing part and/or tank or bag containing the fluid, is held non-reciprocating by the nebulizer, in particular by an inner part thereof, and/or wherein the reservoir, in particular its tank or bag, is fluidically connected or connectable via a preferably flexible fluid connection and/or via the connector with the conveying element and/or the fluid pump. This allows a minimization of the mass which is to be moved together with the reciprocating conveying element and, thus, supports easy operation and/or precise metering and/or a compact construction.

According to another aspect of the present invention, the tank or bag is preferably curved/bent in its main extension, preferably around an axis extending vertically/transversally to the main extension, in particular around the central axis of the reservoir, preferably forming a cylindrical arrangement. This allows a very compact and simple construction and/or a high volume.

According to a further aspect of the present invention, the reservoir comprises preferably a flexible fluid connection and a connector for fluidically connecting the tank or bag of the reservoir to the nebulizer. In particular, the preferably flexible fluid connection connects fluidically the tank or bag with the connector, mostly preferred independently from a movement of the connector relative to the tank or bag. This allows a simple construction and decoupling of the tank or bag from any movement of the conveying or pump element and, thus, a reduction of the mass to be moved during pumping or nebulization.

Preferably, the reservoir or tank or bag comprises multiple compartments, in particular wherein the compartments are arranged side by side/next to each other and/or wherein the compartments are spaced apart in circumferential direction of the reservoir to one another. This allows curving/bending of the tank or bag, in particular without kinking the compartments.

Preferably, the reservoir or tank or bag comprises separate compartments for different fluids. This allows mixing of the different fluids just before use so that mixtures of fluids can be nebulized that are not long-term stable.

Preferably, the bag is formed by sheets and/or sheet material that is/are welded together. This allows an easy and cheap and/or optimized production.

The different aspects mentioned above and the aspects described in the claims and in the following description can be realized independently from each other and in any combination.

BRIEF DESCRIPTION OF THE DRAWING

Further advantages, features, characteristics and aspects of the present invention will become apparent from the claims and the following description of preferred embodiments with reference to the drawings. It shows:

DETAILED DESCRIPTION

Figure 1:
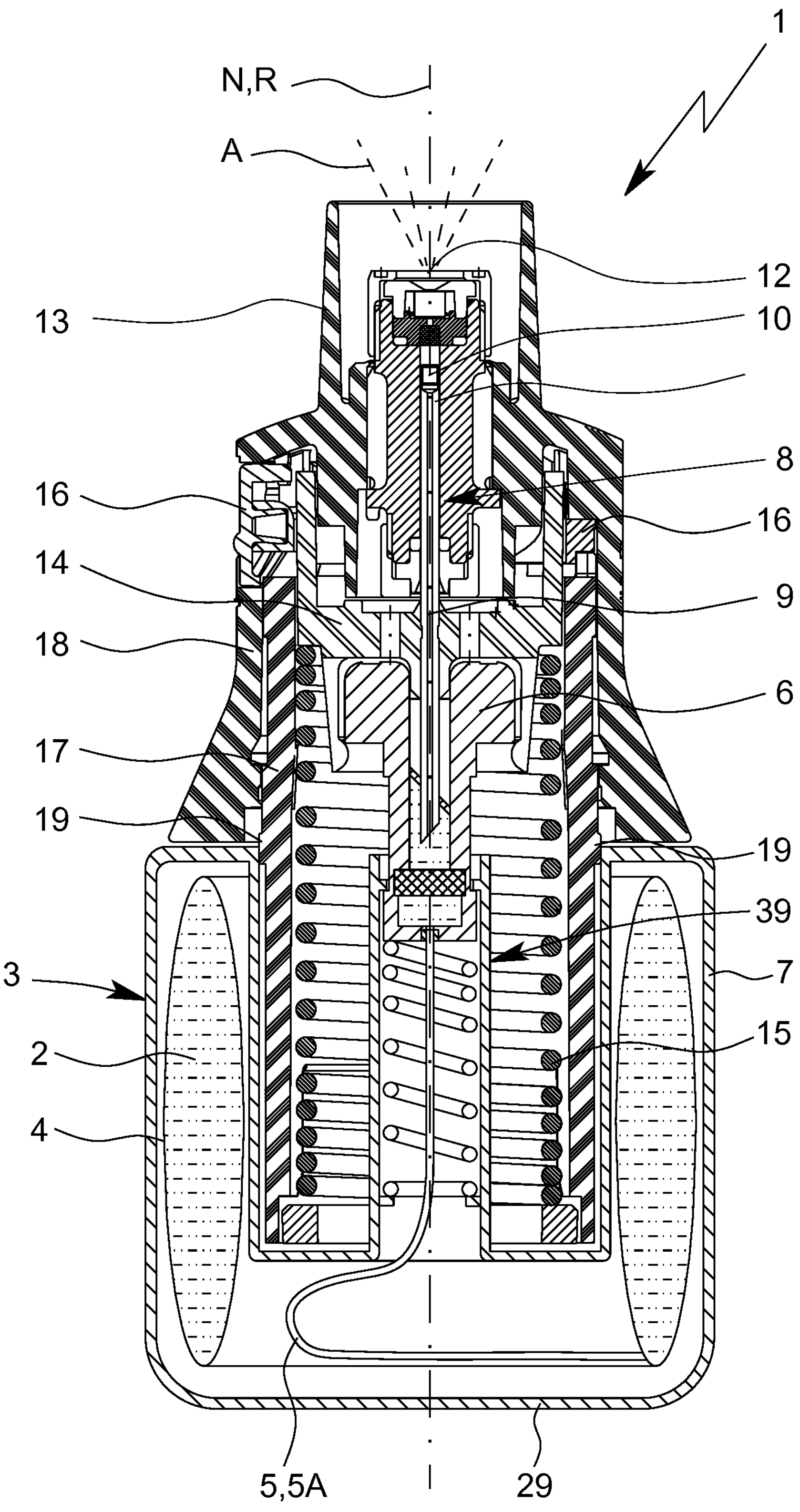
FIG. 1 a schematic section of a nebulizer according to a preferred embodiment of the present invention in a non-tensioned state.

In the Figures, the same reference numerals are used for identical or similar parts, resulting preferably in corresponding or comparable properties and advantages, even if the associated description is not repeated.

Figure 2:
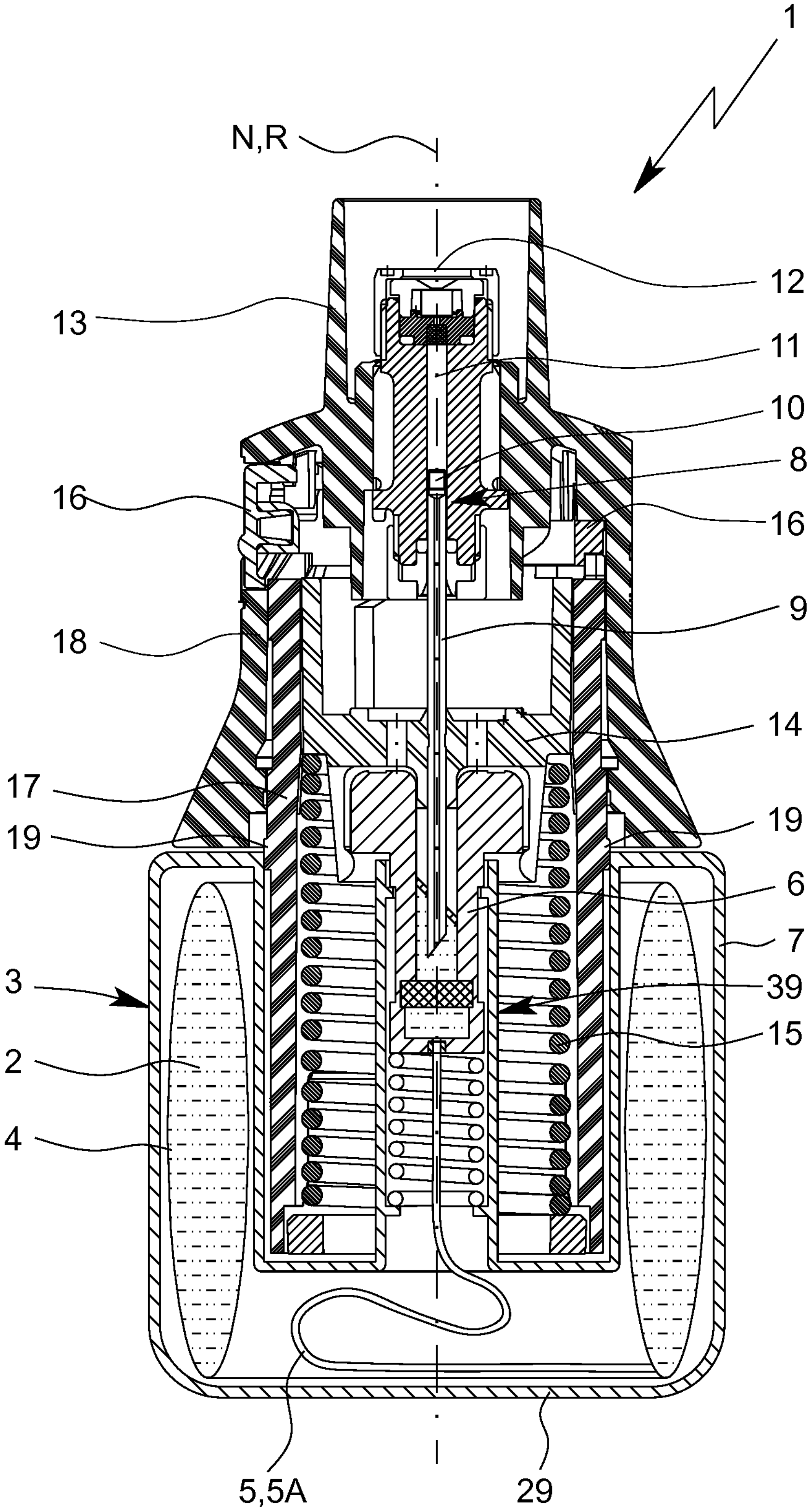
FIG. 2 a schematic section of the nebulizer in a tensioned state.

FIGS. 1 and 2 show a nebulizer 1 according to the present invention for atomizing or nebulizing a fluid 2, particularly a pharmaceutical composition, medicament or the like, diagrammatically shown in a non-tensioned state (FIG. 1) and in a cocked or tensioned state (FIG. 2). The nebulizer 1 is constructed in particular as a portable inhaler and preferably operates only mechanical and/or propellant-free.

When the fluid 2, preferably a liquid, more particularly a pharmaceutical composition, is nebulized, an aerosol A (FIG. 1) is formed or dispensed, which can be breathed in or inhaled by a user. Usually the inhaling is done at least once a day, more particularly several times a day, preferably at set intervals, depending on the complaint or illness from which a patient is suffering.

The nebulizer 1 comprises or is provided with or adapted to receive a preferably replaceable reservoir 3 containing the fluid 2, which is to be nebulized.

Figure 3:
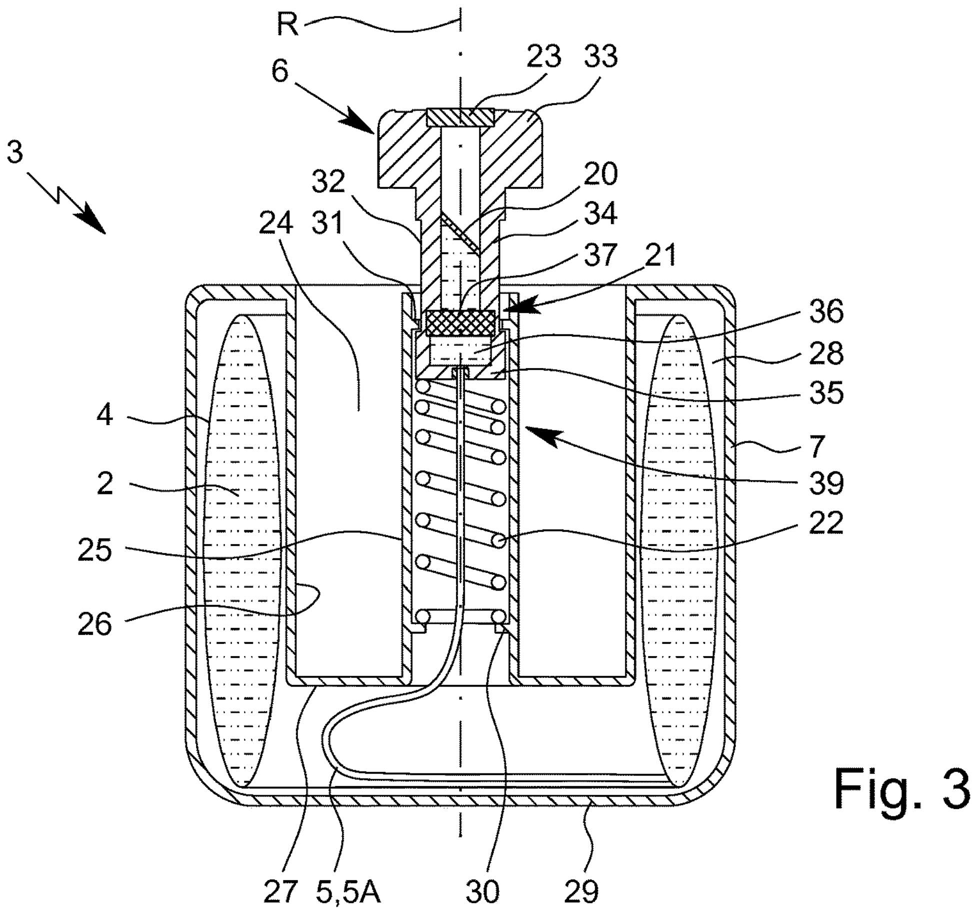
FIG. 3 a schematic section of a preferred embodiment of a reservoir of the nebulizer.

A preferred embodiment of the reservoir 3 is shown schematically in FIGS. 1 and 2 and in the schematic section of FIG. 3.

The nebulizer 1 or reservoir 3 preferably comprises a tank or bag 4 containing the fluid 2 to be nebulized. Preferably the tank/bag 4 is flexible or collapsible so that the term "bag" is used in the following. However, the reservoir 3 could use a rigid tank 4 alternatively.

The bag 4 contains the fluid 2 preferably without any gas or air bubbles and/or without any pressure and/or propellant. Thus, the withdrawal of the fluid 2 is preferably independent from the spatial orientation of the reservoir 3.

Preferably, the reservoir 3 or bag 4 contains multiple doses of fluid 2 or active substance in particular sufficient to provide at least 50 or 100 and/or up to 150 or 200 or more dosage units or doses, for example, i.e. to allow at least 100 and/or up to 200 sprays or applications. The reservoir 3 or bag 4 holds preferably a (maximum) volume of more than 30 ml or about 40 ml to 100 ml.

Further, the number of doses contained in the reservoir 3 or bag 4 and/or the total volume of the fluid 2 contained in the reservoir 3 or bag 4 can vary depending on the fluid 2 or respective medicament and/or depending on the reservoir 3 or bag 4 and/or depending on the necessary medication or the like.

Preferably, the nebulizer 1 is adapted to nebulize a dose of 1 to 100 microliters of fluid 2, even more preferably a dose of 5 to 50 microliters or more, within one actuation/use of the nebulizer 1/within one spray/aerosol delivery/dispension.

Preferably, the reservoir 3 or bag 4 can be replaced or exchanged, wherein the total number of uses of the nebulizer 1 and, thus, the number of reservoirs 3 or bags 4, which can be used with the same nebulizer 1, is preferably restricted, e.g. to a total number of four, five or six reservoirs 3. WO 2012/162305 A1 discloses additionally such a restriction of the total number of reservoirs 3 or bags 4 which can be used with the same nebulizer 1.

The reservoir 3 preferably comprises a flexible/bendable/kink-resistant fluid connection 5 and/or a connector 6 for fluidically connecting the reservoir 3 or bag 4 to the nebulizer 1.

Preferably, the reservoir 3 is at least essentially cylindrical and/or cap-like.

In particular, the reservoir 3 is at least essentially rotationally symmetric and/or comprises a central/main axis R.

The reservoir 3 comprises preferably a housing part 7, preferably wherein the housing part 7 is rigid and/or essentially cylindrical and/or cap-like.

Preferably, the housing part 7 comprises or forms an exterior housing of the reservoir 3. In particular, the housing part 7 forms part of an exterior housing of the nebulizer 1.

In particular, the housing part 7 is at least essentially rotationally symmetric.

Preferably, the axis R extends centrally through the reservoir 3, in particular the housing part 7, and/or forms a longitudinal/rotation axis of the reservoir 3, in particular the housing part 7.

Preferably, the bag 4 is located or arranged within and/or held by the housing part 7, in particular in an immovable manner.

Figure 11:
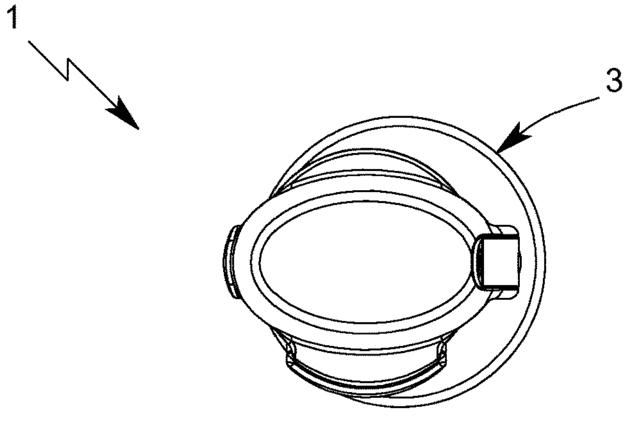
FIG. 11 a top view of the nebulizer according to FIG. 9.

The nebulizer 1 is preferably at least essentially cylindrical and/or elongated/longitudinal and/or comprises preferably a main/central/longitudinal axis N, in particular wherein the central axis N of the nebulizer 1 corresponds to the central axis R of the reservoir 3 (like in the embodiment according to FIG. 1) or is parallel to and/or radially spaced apart from the central axis R of the reservoir 3 (FIG. 11, for instance, shows a nebulizer wherein the central axis R of the reservoir 3 is parallelly/radially spaced apart from the central axis N of the nebulizer 1). However, other constructional solutions are possible as well.

The reservoir 3 or housing part 7 is preferably mechanically connectable or connected to the nebulizer 1, in particular in a detachable and/or form-fit manner.

The nebulizer 1 comprises a delivery mechanism, preferably a pressure generator or fluid pump 8, for conveying and nebulizing the fluid 2, particularly in a preset and optionally in an adjustable dosage amount.

In particular, the pressure generator or fluid pump 8 withdraws or sucks fluid 2, namely a dose of the fluid 2, from the reservoir 3 or its bag 4, preferably when cocking or tensioning the nebulizer 1. Then, the withdrawn fluid 2 or dose of fluid 2 is dispensed, in particular pressurized and/or nebulized, preferably in a second step (dispensing step) after tensioning or nebulization process.

The nebulizer 1 or pressure generator/fluid pump 8 preferably comprises a conveying element 9, here a conveying tube, capillary or the like, for fluidically connecting the nebulizer 1 or pressure generator/fluid pump 8 with the reservoir 3, bag 4, fluid connection 5 or connector 6 and/or for conveying the fluid 2.

The nebulizer 1 or pressure generator/fluid pump 8 preferably comprises a non-return valve 10, a pressure chamber 11 and/or a nozzle 12 for pumping and/or nebulizing the fluid 2, in particular for nebulizing the respective fluid dose as an aerosol A, preferably into a mouthpiece 13 of the nebulizer 1.

The nebulizer 1 or fluid pump 8 preferably comprises a holder 14 for mechanically holding the connector 6, in particular when fluidically connected to the conveying element 9. In particular, the holder 14 is rigidly connected to or with the conveying element 9 or vice versa.

Preferably, the conveying element 9 is moveable axially and/or stroke-like, here in FIGS. 1 and 2 up and down or in a reciprocating manner, in particular together with the holder 14 and/or relative to or within the nebulizer 1 and/or relative to or within the reservoir 3, in particular bag 4, when using the nebulizer 1, in particular for conveying or pumping the fluid 2.

The nebulizer 1 or fluid pump 8 preferably comprises an energy store or drive, here realized as drive spring 15, for driving or pumping, in particular for sucking dose-wise the fluid 2 into the pressure chamber 11 and/or for pressurizing or discharging the respective dose of the fluid 2.

The nebulizer 1 or fluid pump 8 preferably comprises a blocking element 16, in particular being connected to or forming a button for preferably manual actuation or depressing.

Preferably, the blocking element 16 can catch and block the energy store or drive, here the drive spring 15, in a tensioned state and can be manually operated to release the holder 14 or drive spring 15 allowing drive spring 15 to expand for pumping or nebulization. However, other constructional solutions are possible.

The nebulizer 1 or fluid pump 8 preferably comprises an inner part 17 which is in particular rotatable relative to the nebulizer 1 or a housing 18 thereof, preferably together with the reservoir 3 or a housing part 7 thereof.

Preferably, the inner part 17 surrounds/encloses the drive spring 15, holder 14, connector 6 and/or conveying element 9, at least partially and/or radially. Mostly preferred, the inner part 17 is embodied as a hollow cylinder.

The housing 18 of the nebulizer 1 preferably forms an upper part and/or the mouthpiece 13 of the nebulizer 1 and/or is preferably formed integrally with the mouthpiece 13. Mostly preferred, the housing 18 comprises or forms an exterior housing of the nebulizer 1 and/or surrounds or encloses the inner part 17.

Preferably, the reservoir 3 or its housing part 7 is connected/connectable to or with the nebulizer 1 or its housing 18 or most preferably its inner part 17, in particular in a detachable and/or form-fit manner.

Preferably, the reservoir 3 or its housing part 7 is rigidly/immovably connected/connectable to the nebulizer 1 or its housing 18/inner part 17 and/or axially, radially and/or circumferentially held by the nebulizer 1 or its housing 18/inner part 17 or vice versa.

In particular, the reservoir 3 or its housing part 7 is connected/connectable to the nebulizer 1 or its housing 18/inner part 17 in such a way that a torque can be transferred from the reservoir 3, in particular its housing part 7, to the nebulizer 1, in particular its inner part 17, or vice versa, in particular such that a rotation of the reservoir 3 relative to the nebulizer 1 or its housing 18 causes a rotation of the inner part 17 relative to the housing 18.

Preferably, the nebulizer 1, in particular its inner part 17, and/or the reservoir 3, in particular its housing part 7, comprise/comprises at least one retaining element 19 so that the reservoir 3 can be attached to the nebulizer 1, preferably inner part 17.

Preferably, the reservoir 3 can be snapped on and/or locked with the nebulizer 1, in particular via the at least one retaining element 19.

The nebulizer 1, holder 14 and/or retaining element(s) 19 are preferably constructed so that the reservoir 3 can be released or exchanged.

In the embodiment shown in FIGS. 1 and 2, the nebulizer 1 or its inner part 17 comprises the at least one retaining element 19. Alternatively or additionally, at least one retaining element 19 or the like can be located at or formed by the reservoir 3 or its housing part 7 or the like.

Preferably, the reservoir 3 is attachable to the nebulizer 1 or secured against (axial) detachment by form-fit or force-fit.

Preferably, the reservoir 3 or housing part 7 forms part of the housing 18 of the nebulizer 1 or extends (/forms an extension to) the nebulizer 1 or the outer shell or housing 18 of the nebulizer 1.

In the shown embodiment, the reservoir 3 or its housing part 7 is arranged at or connectable to the nebulizer 1 or inner part 17 at an end opposite to the dispensing end or mouthpiece 13.

The reservoir 3 or housing part 7 preferably forms a cap-like or lower housing part and/or fits around or over a lower free end portion of the nebulizer 1 or inner part 17 or drive spring 15.

Mostly preferred, the reservoir 3 or housing part 7 comprises or forms an axial end and/or a bottom of the nebulizer 1, preferably opposite to the dispending end or mouthpiece 13 of the nebulizer 1.

When the reservoir 3 is attached to the nebulizer 1, the holder 14 preferably holds the connector 6 so that the conveying element 9 fluidically connects the reservoir 3, its bag 4 or the connector 6 to the nebulizer 1 or pressure generator/fluid pump 8.

Preferably, the housing 18/inner part 17 holds the reservoir 3 or its housing part 7, when the reservoir 3 is attached to the nebulizer 1.

Preferably, the conveying element 9 penetrates into or pierces the connector 6, in particular through a closure or septum 20 or the like, in particular in order to fluidically connect the reservoir 3 to the nebulizer 1, i.e. its fluid pump 8.

Mostly preferred, the fluid connection between the reservoir 3 and the nebulizer 1, in particular the pressure generator/fluid pump 8, is established by connecting the connector 6 to the nebulizer 1, in particular to the pressure generator/fluid pump 8 and/or conveying element 9.

In particular, a mechanical connection between the reservoir 3 and the nebulizer 1 is additionally established by connecting the housing part 7 of the reservoir 3 to the housing 18/inner part 17 of the nebulizer 1.

When the drive spring 15 is axially tensioned in the tensioning process or during cocking, the holder 14, preferably together with the connector 6 and the conveying element 9, is moved axially (i.e. downwards in the drawings) and fluid 2 is withdrawn or sucked out of the bag 4 into the fluid pump 8 or its pressure chamber 11 through the non-return valve 10.

During this tensioning process, the nozzle 12 preferably acts as a throttle with high flow resistance so that the desired filling of the chamber 11 is achieved.

In the end position, the holder 14 is preferably caught by the blocking element 16 so that the drive spring 15 is kept compressed. Then, the nebulizer 1 is in the cocked or tensioned state, as shown in FIG. 2.

During the subsequent relaxation in the dispensing or nebulization process, i.e. after actuation or pressing of the blocking element 16, the fluid 2 in the pressure chamber 11 is put under pressure as the conveying element 9 with its now closed non-return valve 10 is moved back towards the pressure chamber 11 (i.e. upwards in the drawings) by the relaxation or force of the drive spring 15, which now acts as a pressing ram or piston. This pressure forces the fluid 2 through the nozzle 12, whereupon the fluid 2 is nebulized into the aerosol A, as shown in FIG. 1, and, thus, dispensed.

Generally, the nebulizer 1 operates with a spring pressure of 5 to 300 MPa, preferably 10 to 250 MPa, on the fluid 2, and/or with a volume of fluid 2 delivered per stroke of 10 to 50 μl, preferably 10 to 20 μl, most preferably about 15 μl.

The fluid 2 is converted into or nebulized as aerosol A, the droplets of which have an aerodynamic diameter of up to 20 μm, preferably 3 to 10 μm.

Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol A, preferably while air can be sucked into the mouthpiece 13 through at least one optional air supply opening (not shown).

Preferably, the nebulizer 1 or drive spring 15 can be manually activated or tensioned or loaded, in particular by manual actuation or rotation of an actuation member, here preferably by rotating the inner part 17, reservoir 3 and/or housing part 7 or any other component, in particular relative to the housing 18 of the nebulizer 1.

The actuation member, preferably the housing part 7 or reservoir 3, can be actuated, here rotated relative to the housing 18, carrying with it or driving the inner part 17.

The inner part 17 acts preferably on a gear or transmission (not shown) to transform the rotation in an axial movement. As a result, the energy store or drive spring 15 is tensioned in the axial direction by means of the gear or transmission formed preferably between the inner part 17 and the holder 14 and/or preferably acting on the holder 14.

During tensioning the connector 6 and holder 14 are moved axially and/or towards the housing part 7 of the reservoir 3, in the drawings downwards, until an end position is reached as shown in FIG. 2. In this activated or tensioned state the drive spring 15 is under tension and can be caught or held by the blocking element 16.

During the nebulizing process the container 3 is moved back into its original position (non-tensioned position or state shown in FIG. 1) by (the force of) the drive spring 15. Thus, the conveying element 9 executes a lifting or stroke or reciprocating movement during the tensioning process and during the nebulizing process.

When the reservoir 3 is mechanically connected to the nebulizer 1, the bag 4 or fluid connection 5 or connector 6 is preferably automatically or simultaneously fluidically connected to the fluid pump 8 or conveying element 9. However, it is also possible that the fluid connection of the reservoir 3 or connector 6 to the nebulizer 1 or conveying element 9 is realized later by or with the first tensioning, i.e. movement of the holder 14 and/or conveying element 9 towards or into the reservoir 3 or connector 6. For both cases, the nebulizer 1 and/or reservoir 3 comprises preferably a holding device 21 for holding and/or guiding the connector 6 so that the desired fluid connection can be ensured or facilitated.

In the present embodiment, the reservoir 3 or its housing part 7 preferably comprises of forms the holding device 21, preferably wherein the connector 6 is held such that it can move axially and/or in a reciprocating manner together with the conveying element 9 and/or holder 14 (in particular at least after mechanic and fluid connection of the connector 6 with the conveying element 9 and holder 14 and/or during normal use of the nebulizer 1).

The reservoir 3 or holding device 21 may be adapted or constructed so that the connector 6 is biased or held in an upper position as schematically shown in FIG. 3 which ensures direct fluid connection of the connector 6 with the nebulizer 1 or conveying element 9 when mechanically connecting the reservoir 3 to the nebulizer 1 even if the nebulizer 1 is in its non-tensioned state and/or the holder 14 is in its axial end position remote from the reservoir 3 as shown in FIG. 1.

In the shown embodiment, the reservoir 3 preferably comprises a biasing device 22, here formed by a spring, in particular a helical spring, for holding, positioning and/or biasing the connector 6 in the upper position or towards the conveying element 9 or fluid pump 8 or in the pumping direction for nebulizing the fluid 2.

The biasing device 22 may support the pressurizing stroke or drive spring 15 as the biasing device 22 acts preferably in the same direction as the drive spring 15, and/or may support connecting the conveying element 9 with the connector 6.

The holding device 21 may comprise or be formed by the biasing device 22 or vice versa.

The holding device 21 preferably forms an axial guide and/or defines preferably axial end positions between which the connector 6 is moveable.

Preferably, the holding device 21 is designed or constructed such that the connector 6 is only axially moveable with a stroke, the length of which is preferably limited to the length of the stroke of the conveying element 9 and/or holder 14 during the tensioning process/during the nebulizing process.

In particular, the holding device 21 is adapted to circumferentially and/or radially hold and/or axially guide the connector 6.

Optionally, the connector 6 is held axially immovable in a first or delivery state and—after mechanic and/or fluidic connection—is released such it can move axially during the tensioning and nebulizing strokes. This initial holding can be provided by the holding device 21 and/or by an additional securing mechanism (not shown) wherein the connector 6 can be held by force-fit or by form-fit Constructional solutions are also possible, wherein the connector 6 is (constantly) rigidly/immovably connected to the holding device 21 and/or housing part 7 and/or wherein the conveying element 9 is axially moved relative to the connector 6 when tensioning and/or actuating the nebulizer 1, as will be described with reference to FIGS. 16 to 18.

Preferably, the connector 6 is provided with a seal or cover 23, in particular in addition to septum 20 or any other closure for ensuring a liquid-tight and, in particular, also gas-tight sealing of the fluid 2 contained in the reservoir 3 before first use. The cover 23 may be formed by a foil, in particular a metallic foil or the like.

If necessary, the cover 23 can be removed manually before first use or can be directly opened or pierced by the conveying element 9 when connecting the reservoir 3 to the nebulizer 1.

Preferably, the reservoir 3 or housing part 7 comprises a preferably annular/ring shaped space or receptacle 24 for (axially) receiving at least part of and/or the axial end of the nebulizer 1 or inner part 17 and/or energy store/drive/drive spring 15.

The receptacle 24 is preferably formed or defined by or between a central portion 25 and/or an inner portion 26 of the reservoir 3, in particular of the housing part 7.

Preferably, the central portion 25 is at least essentially cylindrical and/or encompasses or forms the holding device 21 and/or biasing device 22.

Preferably, the inner portion 26 is at least essentially cylindrical and/or encompasses the central portion 25, the holding device 21 and/or the biasing device 22.

Preferably, the inner portion 26 is radially spaced from central portion 25 so that the receptacle 24 is formed between the portions 25 and 26 and is preferably ring-like.

The receptacle 24 is preferably axially restricted or closed by an end portion 27 which interconnects preferably the portions 25 and 26 and/or comprises or forms an axial end or bottom of the receptacle 24.

The reservoir 3 or housing part 7 preferably comprises or forms an in particular annular/ring shaped space 28 for receiving the bag 4.

Preferably, the space 28 is formed between the (outer shell or at least essentially cylindrical wall of) the housing part 7 and the inner portion 26.

The space 28 is preferably at least essentially cylindrical, annular or ring-like.

The space 28 preferably encompasses the receptacle 24, holding device 21 and/or biasing device 22, in particular radially. In particular, the space 28 extends around the receptacle 24, holding device 21 and/or biasing device 22, most preferred in an annular or ring shaped manner.

The space 28 is preferably arranged at a radial distance greater than the radial extension of the connector 6, holding device 21, biasing device 22, receptacle 24, energy store or drive spring 15 and/or inner part 17.

The reservoir 3 or housing part 7 preferably comprises an end face, axial end or bottom 29 which axially defines or closes the outer or circumferential shell of the reservoir 3 or housing part 7.

The reservoir 3, housing part 7, biasing device 22 or central portion 25 preferably comprises a stop 30 for axially bearing one end of the spring of the biasing device 22. The stop 30 can be formed integrally with the central portion 25 or the like.

The other end of the spring acts preferably on the connector 6 for axially biasing the connector 6 upwards or towards the holder 14 or conveying element 9 or fluid pump 8.

Generally, the terms "radial" and "axial" relate preferably to the main or central axis N of the nebulizer 1 and/or to the main or central axis R of the reservoir 3 which are/is preferably formed or defined by the reciprocating movement and/or by the main longitudinal extension of the nebulizer 1 and/or reservoir 3 and/or the main direction of nebulization.

The reservoir 3, holding device 21 or central portion 25 preferably comprises an engagement element 31, such as a nose or the like, which protrudes radially into a recess 32, such as an axial slit, formed at or by the connector 6 so that the connector 6 is axially moveable between two axial end positions. Preferably, the holding device 21 comprises or provides this engagement or axial guidance.

The connector 6 preferably comprises a head 33, a shaft 34 and/or an (axial) end 35, preferably wherein at least the end 35 is arranged and/or guided within the holding device 21.

The connector 6 or its shaft 34 is preferably hollow and/or allows an axial fluidic connection between the bag 4 or fluid connection 5 on one hand and the fluid pump 8 or conveying element 9 on the other hand in the fluidically connected state.

Preferably, the bag 4, fluid connection 5 or connector 6 comprises a mixing chamber 36 for mixing different fluids 2 which will be explained later with reference to other embodiments shown in FIGS. 4 and 5. In the embodiment shown in FIGS. 1 to 3, the mixing chamber 36 is integrated in the connector 6 or its shaft 34.

Preferably, the reservoir 3, bag 4, fluid connection 5 or connector 6 comprises an optional filter 37 for filtering the fluid 2 before discharging the fluid 2 to or into the fluid pump 8 or conveying element 9. In the shown embodiment, the filter 37 is located in the connector 6 or its shaft 34 and/or downstream to the mixing chamber 36, which is preferably adapted to slow down the fluid 2 before entering the filter 37.

Optionally, the filter 37 is an air trap and/or hydrophobic so that any gas bubble would be retained.

When the reservoir 3 is connected with the nebulizer 1, the connector 6 is preferably held by the holder 14, in particular via snap arms or the like. In the connected state, the conveying element 9 has opened or pierced the seal or cover 23 and/or septum 20 so that the reservoir 3 or bag 4 is fluidically connected via the fluid connection 5, the connector 6, the optional mixing chamber 36, the optional filter 37 and/or the hollow shaft 34 to the conveying element 9 and, thus, to the pressure generator or fluid pump 8.

The bag 4 is preferably flat and/or preferably extends in an annular and/or circumferential direction within the housing part 7 or its outer shell and/or within the space 28.

Preferably, the bag 4 is curved/bent in its main extension, i.e. here in circumferential direction, and/or around the central axis R of the reservoir 3 and/or around the central axis N of the nebulizer 1.

Preferably, the annular or circumferential extension of the bag 4 is larger than its axial extension and/or than the axial extension of the reservoir 3 or housing part 7.

Preferably, the bag 4 collapses when the fluid 2 is withdrawn or delivered to the fluid pump 8. However, it is also possible that the tank or bag 4 is rigid, semi-rigid or non-collapsible, but provided with an aeration.

According to an alternative embodiment, the reservoir 3 or bag 4 can be kept or set under pressure—in particular permanently or at least temporarily during fluid withdrawal—and the stroke-like movement can open or control a valve and/or move the conveying element 9 relative to or within the connector 6 for allowing a controlled dispense of a dose of fluid 2 from the reservoir 3/bag 4, in particular similar as described in WO 2010/094305 A1.

Optionally, the collapse of the bag 4 can be supported by applying a pressure and/or providing a respective device or component, such as a spring or another elastic component inside or outside the bag 4, so that withdrawal of a dose of fluid 2 from the bag 4 by the fluid pump 8 is supported or facilitated. Such an embodiment will be described with reference to FIG. 8.

Optionally, the bag 4 can be exchanged after use so that the reservoir 3 can be re-used with a new bag 4. However, it is also possible and preferred that the reservoir 3 together with its bag 4 is for single use only.

The bag 4 contains the fluid 2 preferably without any gas or air bubbles and/or without any pressure and/or propellant.

Preferably, the filling level is visible from outside (in particular when the tank or bag 4 is rigid or semi-rigid). Alternatively, the filling level of the reservoir 3 can be noticed indirectly by the deformation or collapse of the bag 4 when the bag 4 is collapsible.

For checking or showing the filling level, the reservoir 3 or housing part 7 may be—at least partially—transparent or provided with a respective window or the like.

Optionally, the tank or bag 4 can form the outer shell of the reservoir 3 and/or the housing part 7, in particular when the tank or bag 4 is rigid or semi-rigid. In this case, a respective aeration is provided, e.g. by a valve, semi-permeable membrane, filter or the like.

Optionally, the reservoir 3 is provided with a defined orientation relative to the nebulizer 1 before connection, with a coding for indicating the type of fluid 2 (medicament) contained in the bag 4, with a label, with a dose indicator and/or the like.

As mentioned before, the fluid connection 5 is preferably at least partially flexible/bendable.

In particular due to its flexibility, the fluid connection 5 can maintain the fluid connection between the connector 6 and the bag 4 independently from an axial movement of the connector 6 relative to the bag 4 and/or even when the connector 6 reciprocates. Preferably, the fluid connection 5 is bendable, in particular without kinking and/or without reducing the inner diameter of the fluid connection 5 by more than 10% of inner diameter when the fluid connection 5 is unbent.

Preferably, the fluid connection 5 comprises or is formed by a flexible tube 5A or the like.

The tube 5A is preferably made of rubber, in particular butyl rubber, and/or (flexible) plastic, in particular thermoplastics and/or thermoplastic elastomers, such as polyamide, polyethylene, polypropylene, polybutylene terephthalate or polyether block amide or the like. Other suitable materials might be used as well.

The inner diameter of the fluid connection 5 or flexible tube 5A is preferably 0.4 to 1.0 mm in order to avoid or minimize the forming of any gas bubbles or foam.

Preferably, the fluid connection 5 or flexible tube 5A extends—in particular some millimeters or at least 1 cm or more—into the bag 4 such that in overhead orientation any small gas bubble in the bag 4 would not be sucked into the fluid connection 5 and the connected fluid pump 8.

Mostly preferred, the flexible tube 5A, in particular one of its axial ends, is laminated into the bag 5, as will be described with references to FIGS. 13 to 15.

The flexible fluid connection 5 allows the stroke-like movement or reciprocating movement of the fluid pump 8 or its piston/conveying element 9 without any respective or axial movement of the tank or bag 4 and, thus without the primary mass of the fluid 2. Thus, the total mass to be moved during each stroke is minimized. This allows a minimization of the required or acting forces and/or supports reliable and precise metering of the fluid 2 so that all doses are at least constant and independent from the filling level of the reservoir 3 or bag 4.

For tensioning the nebulizer 1 or the drive spring 15, the reservoir 3 or housing part 7 is manually rotated, preferably relative to the housing 18. In order to facilitate this manual operation and/or intuitive handling, the reservoir 3 or housing part 7 may be provided with a grip portion, such as an indention or protrusion, and/or with an indication, such as an arrow, or the like.

As already mentioned, the connector 6 can be stationary or formed part of the housing part 7. In this case, the connector 6 comprises preferably a sealing, such as an elastic material and/or O-ring, which seals against the moveable conveying element 9. For this purpose, also a plug made of rubber or the like could be used for sealing the reservoir 3/connector 6 and which might be covered by a protection cap, e.g. made of aluminum or the like. For use, the cap could be opened or removed by the user. Then, the reservoir 3 is connected to the nebulizer 1 and the conveying element 9 pierces the plug. This plug serves also as a sealing during the stroke movement of the conveying element 9. An embodiment showing a stationary connector 6 will be described with reference to FIGS. 16 to 18.

According to another modification (not shown), the reservoir 3 or its tank/bag 4 could be arranged at least partially around the fluid pump 8 or its pump/pressure chamber 11 and/or in the height or axial location of the fluid pump 8 or its pump/pressure chamber 11 so that only a very low pressure difference is necessary to suck a dose of the fluid 2 out of the reservoir 3 into the fluid pump 8 or its pump/pressure chamber 11. This facilitates or ensures a very precise metering with doses of constant volume. Further, this may support priming, i.e. multiple pumping processes (tensioning strokes and nebulization strokes) to prepare the nebulizer 1 before first use, in particular to replace any air in the fluid system by the fluid 2.

In the following, other preferred embodiments of the reservoir 3 will be described with reference to FIGS. 4 and 5, wherein only relevant differences or new aspects/features are described or emphasized and wherein the previous explanation and description applies preferably additionally or correspondingly even without repetition. In particular, the reservoir 3 according to FIGS. 4 and 5 might comprise one or several features described with reference to FIGS. 1 to 3 and can be used with the nebulizer 1 described with reference to FIGS. 1 and 2.

Figure 4:
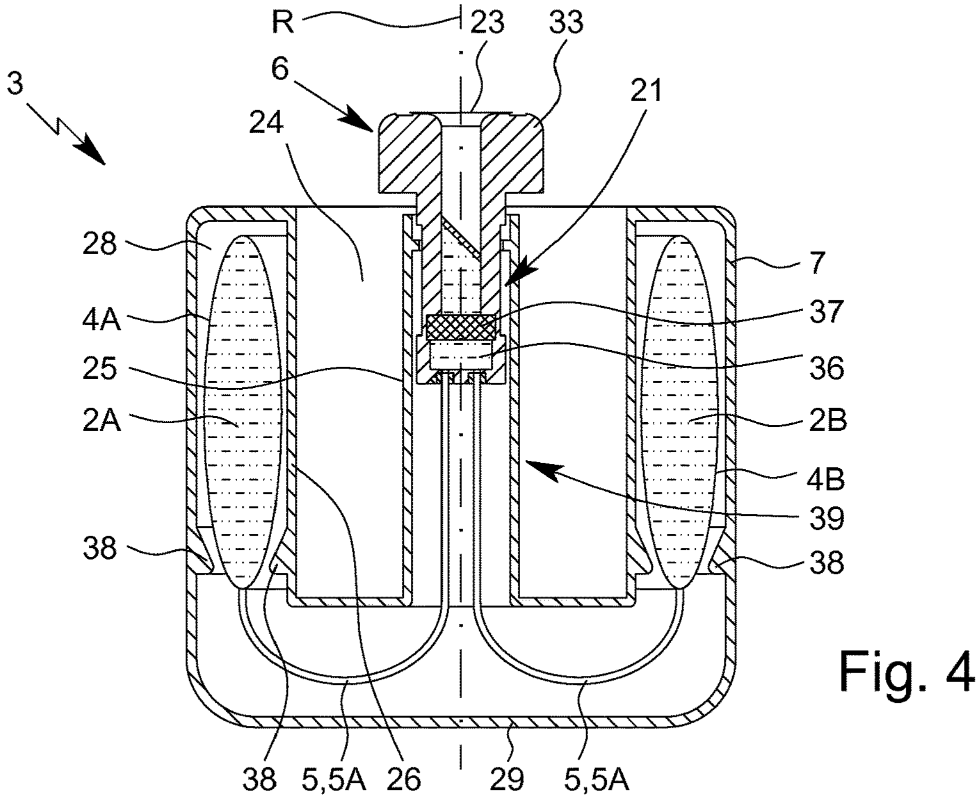
FIG. 4 a schematic section of another embodiment of the reservoir.

FIG. 4 shows in a schematic section similar to FIG. 3 another embodiment of the reservoir 3. FIG. 4 shows the reservoir 3 with the connector 6 in a retracted position, in particular in a position corresponding to the tensioned state, whereas FIG. 3 shows the connector 6 in the protruding position, in particular corresponding to the axial position in the non-tensioned state of the nebulizer 1.

In the embodiment according to FIG. 4, the reservoir 3 preferably comprises multiple, in particular two bags 4A and 4B, preferably with different fluids 2A and 2B.

Preferably, each bag 4A, 4B is fluidically connected via a separate flexible fluid connection 5A, 5B to the mixing chamber 36 and/or common connector 6. Thus, the different liquids 2A and 2B are mixed preferably just before use. This allows the nebulization of mixtures of fluids 2A, 2B which are not long-term stable.

Alternatively, the bag 4 can comprise multiple, here two, separate compartments 4A and 4B, preferably with the different fluids 2A and 2B. In particular in this case, each compartment 4A and 4B is fluidically connected via a separate flexible fluid connection 5 to the mixing chamber 36 or connector 6 or conveying element 9. Thus, similar advantages can be achieved as in the case of separate bags 4A and 4B. An embodiment of a bag 4 with multiple compartments will be described with reference to FIGS. 13 to 18.

In the embodiment according to FIG. 4, the different fluids 2A and 2B are mixed in the reservoir 3 or connector 6. However, it is also possible to mix the different fluids 2A, 2B in the nebulizer 1 or fluid pump 8. For this purpose, the connector 6 can provide separate fluid ports for the different fluidic connections 5A, 5B or different fluids 2A, 2B, wherein the nebulizer 1 or fluid pump 8 can fluidically connect these ports via a common conveying element 9 with two separate fluid lines or via two separate conveying elements 9. However, other constructional solutions are possible as well.

Preferably, valves, in particular non-return valves or check valves, are provided for the different fluids 2A, 2B and/or separate bags/compartments 4A, 4B and/or fluidic connections 5A, 5B so that the different fluids 2A and 2B cannot mix and flow back in any one of the fluidic systems/connections 5/compartments or bags 4A, 4B.

In the shown embodiment, the reservoir 3 or outer housing 7 and/or inner portion 26 may comprise a holding element 38 such as a protrusion or the like, for holding or securing the bag 4 or bags 4A, 4B in the reservoir 3, housing part 7 and/or space 28.

Figure 5:
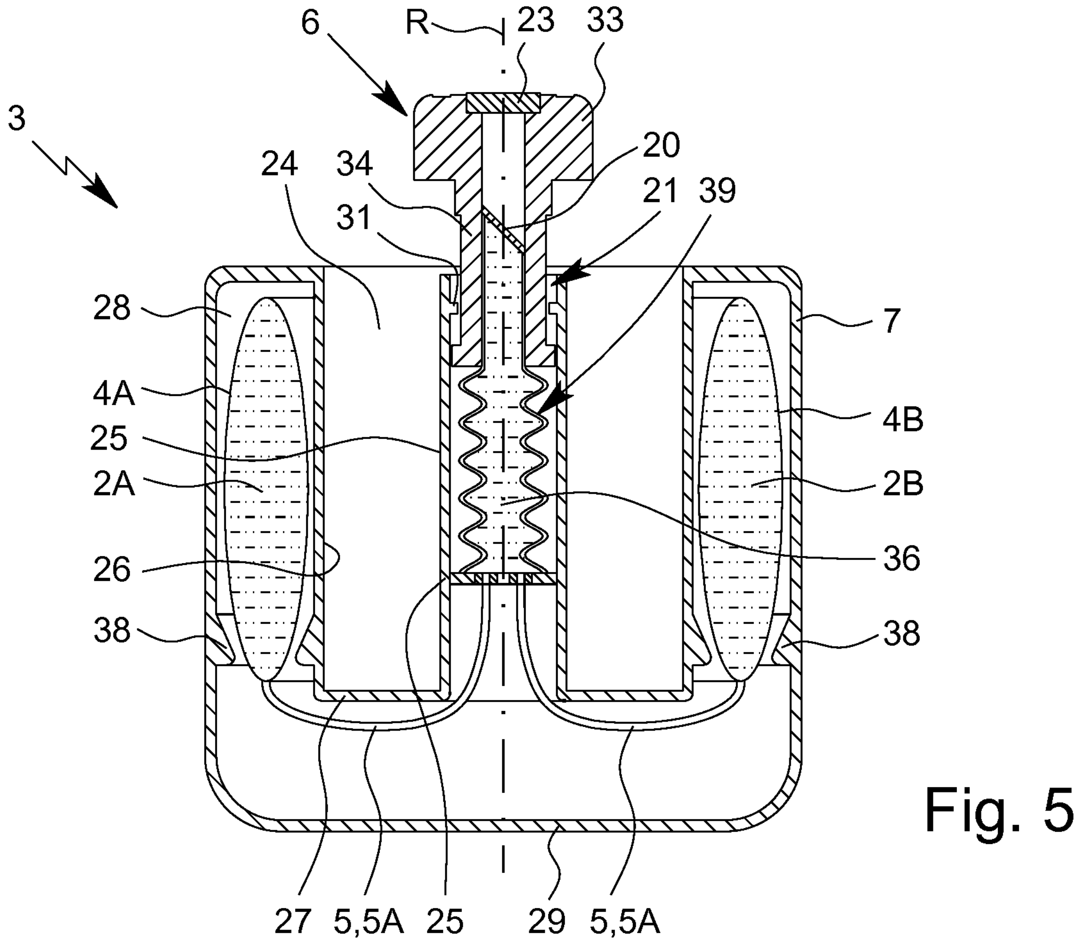
FIG. 5 a schematic section of a further embodiment of the reservoir.

FIG. 5 shows in a similar schematic section a further embodiment of the reservoir 3. This reservoir 3 is constructed quite similar to the embodiment according to FIG. 4, but comprises a pump device 39, such as a bellows or the like, for pre-pressurizing the fluid 2 or fluids 2A, 2B or for delivering or pumping the fluid 2 or fluids 2A, 2B to the fluid pump 8.

In particular, the pump device 39 is actuated by the reciprocating or stroke-like movement, in particular of the connector 6, during the tensioning process and nebulizing process.

Preferably, the pump device 39 is located stream-up of the connector 6 and/or fluidically connected with the connector 6 and/or biases the connector 6 into an axial position, here the protruding or upward position, and/or forms the mixing chamber 36.

Preferably, the connector 6, the holding device 21, the biasing device 22 and/or the pump device 39 are arranged centrally in or at the reservoir 3, housing part 7, receptacle 24, central portion 25, inner portion 26 and/or space 28. In particular, the central axis N of the nebulizer 1 and/or the central axis R of the reservoir 3 run(s) centrally through the connector 6, the holding device 21, the biasing device 22 and/or the pump device 39. However, other constructional solutions are also possible and will be described later.

Preferably, the pump device 39 forms the biasing device 22 and/or holding device 21 or vice versa.

It has to be noted that the reservoir 2 with the pump device 39 can be provided optionally only with one single bag 4, fluid 2 and/or flexible fluid connection 5 similar to the embodiment according to FIG. 3.

Further, it has to be noted that the pump device 39 is preferably provided with respective throttles or valves at the inlet and/or outlet side in order to generate the desired pumping or pressurizing effect.

Generally, the holding device 21 holds the connector 6 preferably in a defined position in a delivery state of the reservoir 3 or before first use or until the reservoir 3 is connected to the nebulizer 1. This defined position may be the protruding position or upward position as shown in FIGS. 3 and 5 or the withdrawn or retracted position as shown in FIG. 4. This holding can be achieved by form-fit or force-fit or by a predetermined breaking point or pull linkage or the like.

Alternatively, the connector 6 might be pulled out of the housing part 7 in the delivery state, even further than in the non-tensioned position (as shown in FIGS. 1, 3 and 5). For example, the holding device 21 can comprise a protrusion (not shown) that needs to be overcome when connecting the reservoir 3 for the first time or a securing element/cuff (not shown) that needs to be detached before connecting the reservoir 3 for the first time.

Preferably, the holding device 21 releases the connector 6 and/or allows a reciprocating movement of the connector 6 after the reservoir 3 or connector 6 has been connected to the nebulizer 1.

Figure 6:
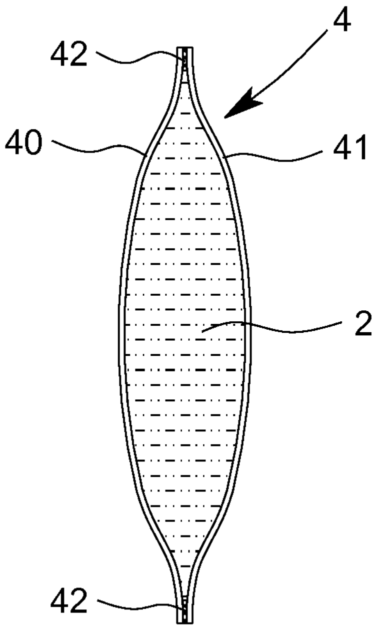
FIG. 6 a schematic section of a bag of the reservoir.

FIG. 6 shows a schematic section of the bag 4 according to a preferred realization. Here, the bag 4 comprises or is made of or consists of (flexible) sheet material. Preferably, the sheet material is of multi-layer construction and/or welded together and/or flexible and/or made at least essentially of plastics.

Preferably, at least one sheet or two sheets 40 and 41 of the sheet material are welded together preferably wherein at least one welding seam 42 is formed. In particular, two welding seams 42 are formed as shown in the schematic section according to FIG. 6. These welding seams 42 extend along the longitudinal sides or edges of the sheet material or sheets 40, 41.

Preferably, the bag 4 is pouch-like and/or essentially or relatively flat. In particular, the term "flat" has to be understood in that the bag 4 has an areal extension in two dimensions wherein these extensions are more than five times greater than the thickness of the bag 4, i.e. than the extension of the bag 4 perpendicular to the areal extension.

Preferably, term "flat" means that the bag 4 comprises a height and/or length that is several times, in particular at least five times, greater than its thickness.

Preferably, the longitudinal edges or seams 42 of the bag 4 are spaced axially when the bag 4 is mounted or arranged in the reservoir 3.

Figure 7:
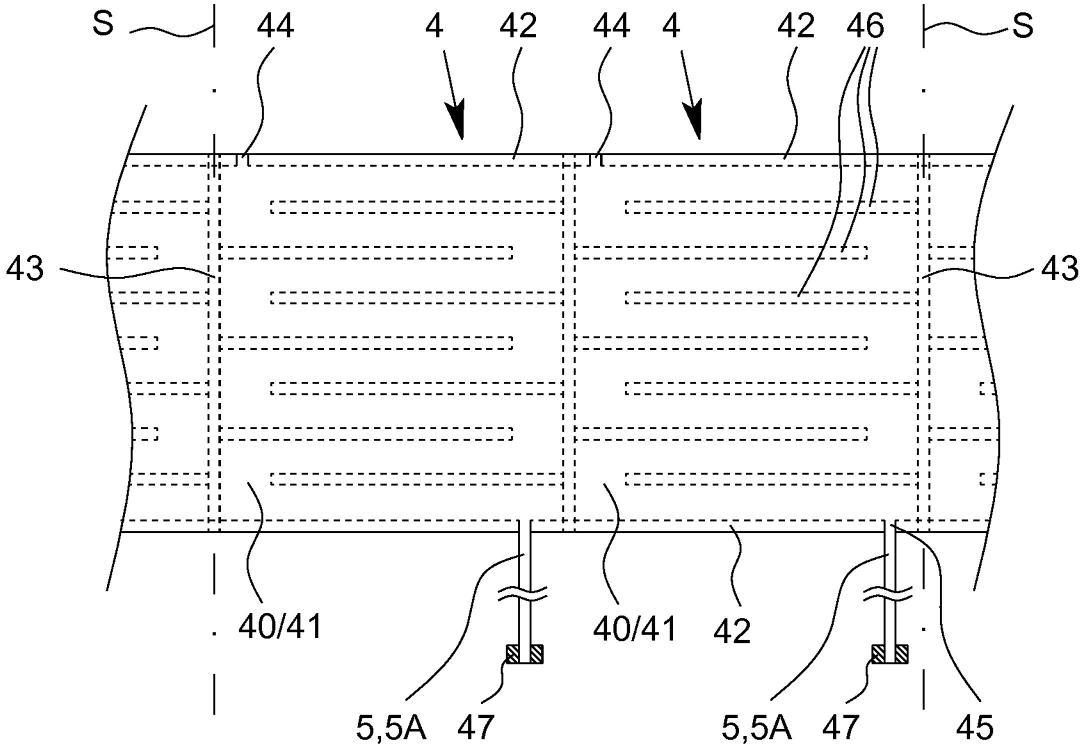
FIG. 7 a schematic view of the production of bags for the reservoir.

FIG. 7 shows in a very schematic view a possible production of the bags 4. The sheet material or sheets 40, 41 are shown from above or a flat side and/or are formed preferably by a continuous stripe or slat or the like.

In addition to one or more longitudinal welding seams 42, transversal welding seams 43 may be provided in particular such that the different bags 4 can be separated along these welding seams 43 or separation lines S as schematically indicated in FIG. 7.

Preferably, the bags 4 are formed as flat, essentially rectangular pouches.

Optionally, the bags 4 or its compartments can be provided with intermediate welding seams 46 which may provide an interdigital or finger like pattern, in particular for guiding the fluid 2 in the respective compartment or bag 4.

The bags 4 are provided preferably with inlets 44 and/or outlets 45 for filling the bags 4 in particular bubble-free with the fluid 2 and/or for aeration.

Preferably, each bag 4 is provided with the associated flexible fluid connection 5, such as a tube 5A, which is fluidically connected to the outlet 45, preferably by gluing, welding or the like.

Mostly preferred, one axial end of the fluid connection 5, in particular the tube 5A, is welded/laminated into the bag 4, sheets 40, 41 and/or seam 42 and/or between the sheets 40, 41.

Preferably, the free end of the fluid connection 5 is provided with a closure, bursting element, valve, septum and/or connecting element 47. Alternatively or additionally, the outlet 45 can be provided with a closure, bursting element, valve or the like.

After filling of the bag 4 with the fluid 2, the bag 4 is closed or sealed, in particular by closing or sealing the inlet 44 and the outlet side, i.e. the outlet 45, the fluid connection 5 and/or connecting element 47 or respective closure or valve.

The bag 4, outlet 45 or connecting element 47 is preferably automatically opened during first use, e.g. when cocking the nebulizer 1 or fluid pump 8, or when the bag 4, fluid connection 5 or connecting element 47 is connected to the connector 6.

Preferably, the reservoir 3 comprises one or more ports for receiving or connecting with the respective connection element 47 in order to allow simple assembly of the reservoir 3.

It is also possible that the connecting element 47 is provided with the septum 20 and/or forms the connector 6 so that the conveying element 9 opens or pierces the connecting element 47 or opens any other kind of closure for establishing the fluidic connection to the associated bag 4.

Preferably, the tank/bag 4 or sheets 40, 41 are made of PE, PP, COC, COP, PVC, glass, PCTFE (ACLAR®) foil, Surlyn® foil, a composite foil including aluminum such as PE/AL/PET, or the like, and/or are coated with $SiO_2$ or the like.

The reservoir 3, bag 4 and/or connector 6 may be provided with a preferably sterile and/or fluid-tight or gas-tight barrier, cover or packaging, preferably of aluminum, PET, $SiO_2$ or the like. The same applies preferably for the nebulizer 1 or its conveying element 9.

For example, the conveying element 9 can be provided at its free end with a cover or plug, e.g. made of rubber or the like, and could be sterilized. When the conveying element 9 is connected to the reservoir 3 or connector 6, the conveying element 9 may pierce the cover/plug so that it is pushed back on the conveying element 9.

The sterile protection of the conveying element 9 and/or reservoir 3 or connector 6 is preferred, in particular if the fluid 2 does not contain any antidegradants/preservatives.

In the following, another preferred embodiment of the reservoir 3 will be described with reference to FIG. 8, wherein only relevant differences or new aspects/features are described or emphasized and wherein the previous explanation and description applies preferably additionally or correspondingly even without repetition. In particular, the embodiment according to FIG. 8 might comprise one or several features of the reservoir 3 described with reference to FIGS. 1 to 7 and can be used with the nebulizer 1 described with reference to FIGS. 1 and 2.

As mentioned before, the reservoir 3 may comprise a pump device 39. Mostly preferred, a pump device 39 is integrated in the reservoir 3.

The optional pump device 39 is adapted to—in particular temporarily—pressurize the fluid 2 in the reservoir 3, in particular in order to help withdrawing the fluid 2 in doses, preferably (only) during tensioning of the nebulizer 1.

Preferably, the pump device 39 is actuated by tensioning of the nebulizer 1 and/or by nebulizing the fluid 2, in particular by the stroke-like movement of the connector 6, i.e. when the connector 6 is moved relative to the housing part 7 and/or the bag 4.

In contrast to the pump device 39 shown in FIG. 5, the pump device 39 shown in FIGS. 1 to 4 and 8 is preferably embodied as an air pump and/or adapted to pressurize the fluid 2 within the bag 4 and/or to increase the pressure in the bag 4, at least temporarily and/or during tensioning of the nebulizer 1 and/or during withdrawal of a dose of the fluid 2.

Mostly preferred, the pump device 39 is adapted to pressurize the air contained in the housing part 7 and/or the space 28.

The pump device 39 preferably comprises or forms a piston/cylinder arrangement, preferably wherein the connector 6, in particular its axial end 35, comprises or forms the piston of the piston/cylinder arrangement and/or wherein the housing part 7, in particular the holding device 21, comprises or forms the cylinder of the piston/cylinder arrangement. With other words, the pump device 39 is preferably formed by the connector 6 and the holding device 21, wherein the connector 6 is axially moveable within the holding device 21 and/or circumferentially and/or radially guided by the holding device 21.

Optionally, a sealing can be provided between the piston and the cylinder. For example, a sealing element 39A, such as an O-ring or the like, could be used, preferably wherein the sealing element 39A is arranged within a groove 39B formed in the piston.

Alternatively or additionally, the inner surface of the cylinder and/or the outer surface of the piston can be provided with a glide agent, such as silicone, grease or the like, in order to reduce friction and/or for sealing.

The pump device 39 works preferably mechanically.

Preferably, the pump device 39 comprises at least one optional air leakage 39C, preferably wherein the air leakage 39C is formed by an opening/hole in the housing part 7, here in the end portion 27.

Preferably, the air leakage 39C connects the space 28 to the atmosphere/environment.

After withdrawing or sucking fluid 2 from the reservoir 3 or its bag 4, the nebulizer 1 is in the tensioned or cocked state and/or is ready for dispensing/nebulization, as mentioned before.

In the tensioned or cocked state of the nebulizer 1, the air pressure within the housing part 7 and/or space 28 and, thus, the pressure of fluid 2 in the bag 4 preferably decreases and/or is compensated relative to the atmosphere, in particular automatically, due to the air leakage 39C.

It is also possible to achieve the desired leakage with a radial play between the pump piston and the cylinder and/or a respective leakage channel or passage, e.g. in the seal 39A.

Preferably, the air leakage 39C or any other air leakage, such as the optional/preferred radial play between the piston and the cylinder, forms a throttle which is dimensioned such that the flow resistance is sufficiently high to create a sufficiently high air pressure during the tensioning stroke and is sufficiently low so that pressurized air can escape relatively quickly in the tensioned state from the housing part 7 or space 28 into the environment. In this way, the air pressure is quickly decreased in the tensioned state to avoid any undesired fluid flow in the tensioned state of the nebulizer 1 before firing (actuating blocking element 16 to initiate nebulization).

Preferably, the reservoir 3, in particular pump device 39, comprises at least one valve 48 for controlling or limiting the (maximum) air pressure and/or for aerating the pump device 39 and/or for preventing any underpressure (negative pressure with respect to the ambient pressure) in the pump device 39. However, the valve 48 is only optional and can be omitted.

The valve 48 forms or comprises preferably an inlet, duckbill or one-way/check valve and/or opens to prevent or at least minimize any underpressure in the pump device 39 and/or housing part 7 and/or space 28 during firing/dispensing, i.e. when the connector 6 moves back from its position shown in FIGS. 2 and 4 to its initial position shown in FIGS. 1, 3, 5 and 8.

Optionally, the valve 48 or another valve of the nebulizer 1, reservoir 3 and/or pump device 39 comprises or forms preferably a control valve for controlling or limiting the air pressure acting on the fluid 2 in the bag 4, preferably to a maximum value above the ambient pressure independently from a filling level of the reservoir 3 or bag 4.

The valve 48 and/or the additional control valve opens preferably when a predetermined or desired air pressure is reached in the pump device 39 and/or housing part 7 and/or space 28. Thus, a defined or maximum air pressure is provided for pressurizing the fluid 2 in the reservoir 3.

Preferably, the reservoir 3, in particular its housing part 7 or bottom 29, comprises an opening 49, in particular wherein the opening 49 (fluidically) connects the space 28 to the atmosphere.

The valve 48 is preferably arranged at and/or attached to the bottom 29 of the reservoir 3, preferably covering the opening 49. In particular, the space 28 is (fluidically) connected to the atmosphere via the valve 48 and the opening 49.

Alternatively and/or additionally to the pump device 39, the reservoir 3 preferably comprises a pressurizing device 50 for pressurizing the fluid 2 in the reservoir 3/bag 4, in particular in order to help withdrawing the fluid 2 in doses, preferably constantly and/or independently from tensioning and/or actuating the nebulizer 1 or reservoir 3. Thus, the withdrawal of the fluid 2 is preferably independent from the spatial orientation of the reservoir 3.

Preferably, the pressurizing device 50 acts mechanically and/or directly on the bag 4.

Mostly preferred, the pressurizing device 50 is arranged within the housing part 7 and/or space 28 and/or directly next to the bag 4.

The pressurizing device 50 presses preferably radially against the bag 4, i.e. its flat—inner and/or outer—side/surface.

Preferably, the pressurizing device 50 comprises or is formed by at least one spring, in particular a leaf spring, preferably wherein the spring is pretensioned against the bag 4 and/or arranged between the bag 4 and the housing part 7.

As the reservoir 3, i.e. its housing part 7, is preferably cylindrical, the pressurizing device 50 might be curved/bent in its main extension and/or around axis R of the reservoir 3 and/or extend in an annular and/or circumferential direction within the housing part 7. For example, the pressurizing device 50 might comprise several springs or spring elements that are curved/bent and/or at least partially distributed over the circumference of the bag 4.

Figure 8:
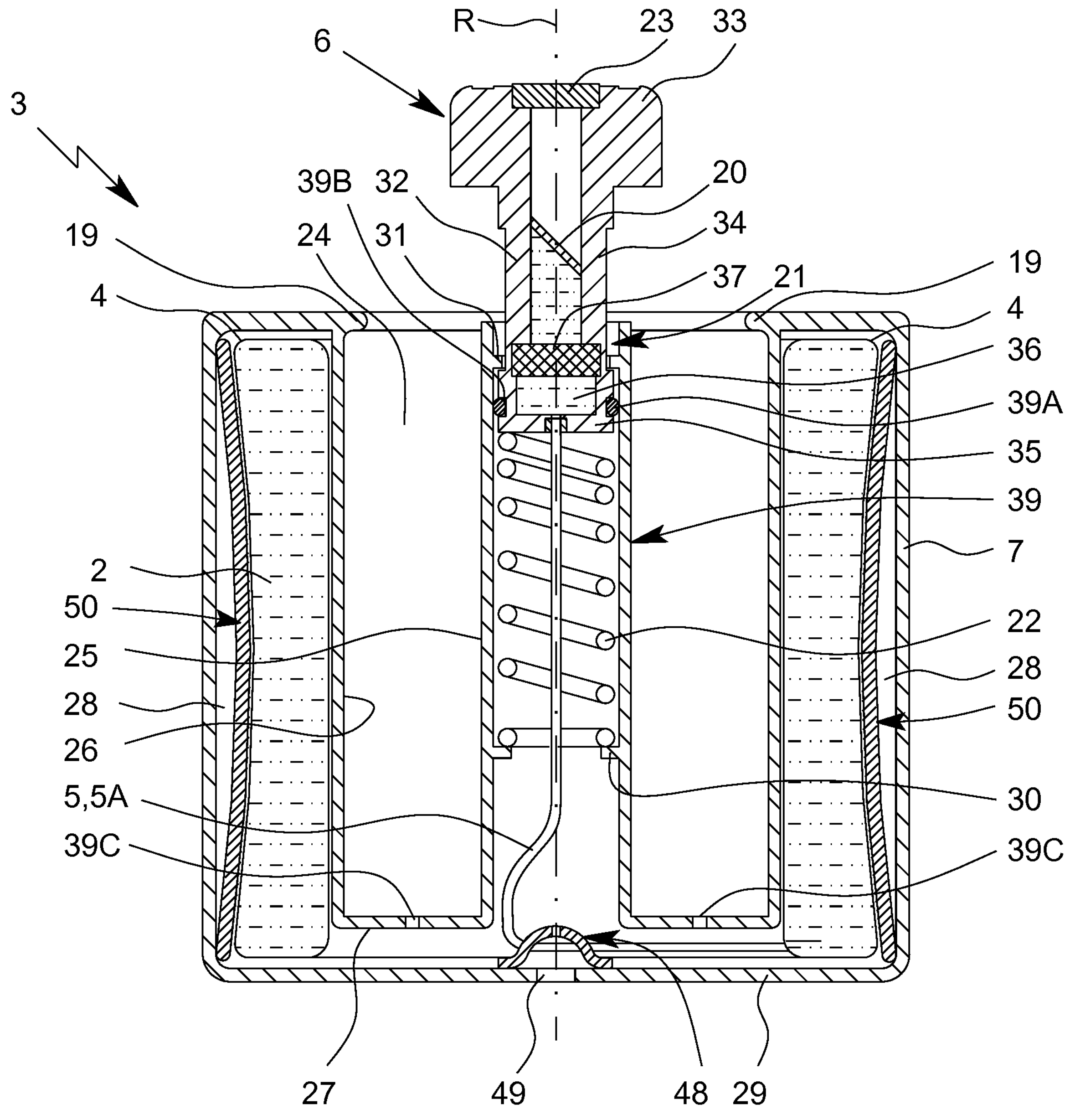
FIG. 8 a schematic section of another embodiment of the reservoir.

In the embodiment shown in FIG. 8, the pressurizing device 50 is arranged on the outer flat side/surface of the bag 4 and/or presses inwardly (with regard to the axis R of the reservoir 3) against the bag 4. However, constructional solutions are also possible, wherein the pressurizing device 50 is—additionally or alternatively—arranged on the inner flat side/surface of the bag 4 and/or presses outwardly (with regard to the axis R of the reservoir 3) against the bag 4. In particular, it is possible that the bag 4 is at least partly clamped between the pressurizing device 50, e.g. two springs or spring elements thereof.

In the following, further preferred embodiments of the nebulizer 1 and reservoir 3 will be described with reference to FIGS. 9 to 18, wherein only relevant differences for new aspects/features are described or emphasized and wherein the previous explanation or description applies preferably additionally or correspondingly even without repetition. In particular, the nebulizer 1 or reservoir 3 according FIGS. 9 to 18 might comprise one or several features of the nebulizer 1 or reservoir 3 described with reference to FIGS. 1 to 8.

As mentioned before, the reservoir 3, in particular its housing part 7, is preferably at least essentially cylindrical and/or comprises a main/central/longitudinal axis R. Further, the nebulizer 1, in particular its housing 18, is preferably at least essentially cylindrical and/or elongated/longitudinal and/or comprises a main/central/longitudinal axis N.

Figure 9:
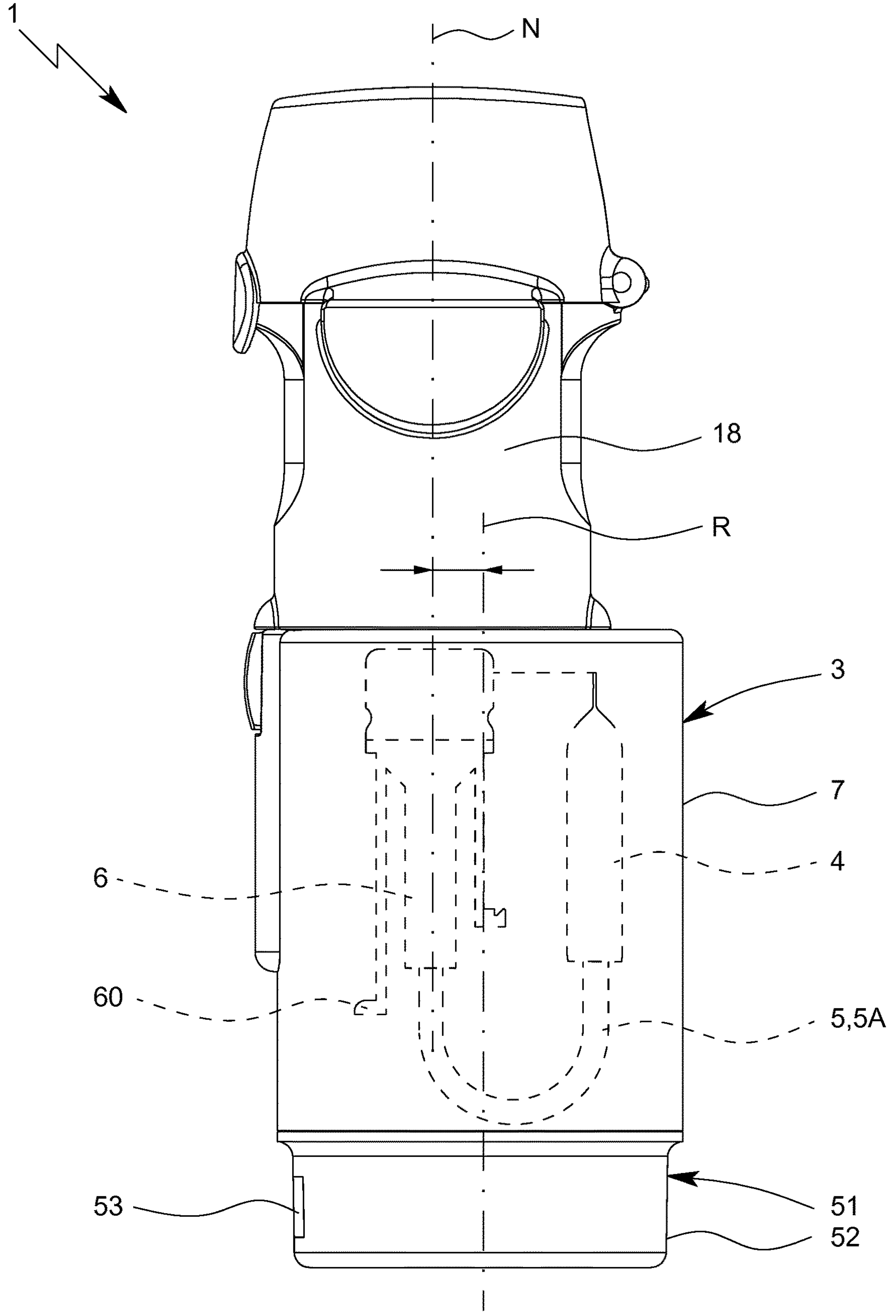
FIG. 9 a side view of another embodiment of the nebulizer.

In contrast to the previous embodiments, the central axis N of the nebulizer 1 according to the present embodiment is preferably spaced apart and/or radially displaced from the central axis R of the reservoir 3, as best seen in FIGS. 9 and 11. In particular, the central axis R of the reservoir 3 is parallel to the central axis N of the nebulizer 1.

In particular, the reservoir 3 is arranged eccentrically and/or (regarding its central axis R) radially displaced relative to the nebulizer 1, in particular its inner part 17 or housing 18.

In particular, the central axis R of the housing part 7 is spaced apart and/or radially displaced from the central axis N of the inner part 17, housing 18 and/or fluid pump 8.

Mostly preferred, the connector 6, holding device 21, biasing device 22 and/or the receptacle 24 are/is eccentrically arranged within the reservoir 3, in particular with regard to the housing part 7 and/or the central axis R of the reservoir 3, and/or concentrically arranged with regard to the central axis N of the nebulizer 1, in particular fluid pump 8, conveying element 9, holder 14, drive spring 15, inner part 17 and/or housing 18, as indicated in FIG. 9 with dashed lines.

In particular, the connector 6, holding device 21, biasing device 22 and/or the receptacle 24 are/is coaxially arranged with the fluid pump 8, conveying element 9 and/or holder 14 of the nebulizer 1.

Due to the eccentrical arrangement of the connector 6 within the reservoir 3, it is possible to eccentrically arrange the bag 4 within the reservoir 3, in particular housing part 7, and/or to eccentrically arrange the reservoir 3, in particular its housing part 7, relative to the nebulizer 1, in particular its inner part 17 and/or housing 18.

In this way, the space in the reservoir 3 is efficiently used.

Further, the manual rotation of the reservoir 3 is facilitated due to the lever caused by the radial distance between the central axis N of the nebulizer 1 and the central axis R of the reservoir 3.

The nebulizer 1 or reservoir 3 preferably comprises an indicator device 51 for counting and/or indicating a number of uses performed or still possible with the reservoir 3 or bag 4.

Figure 10:
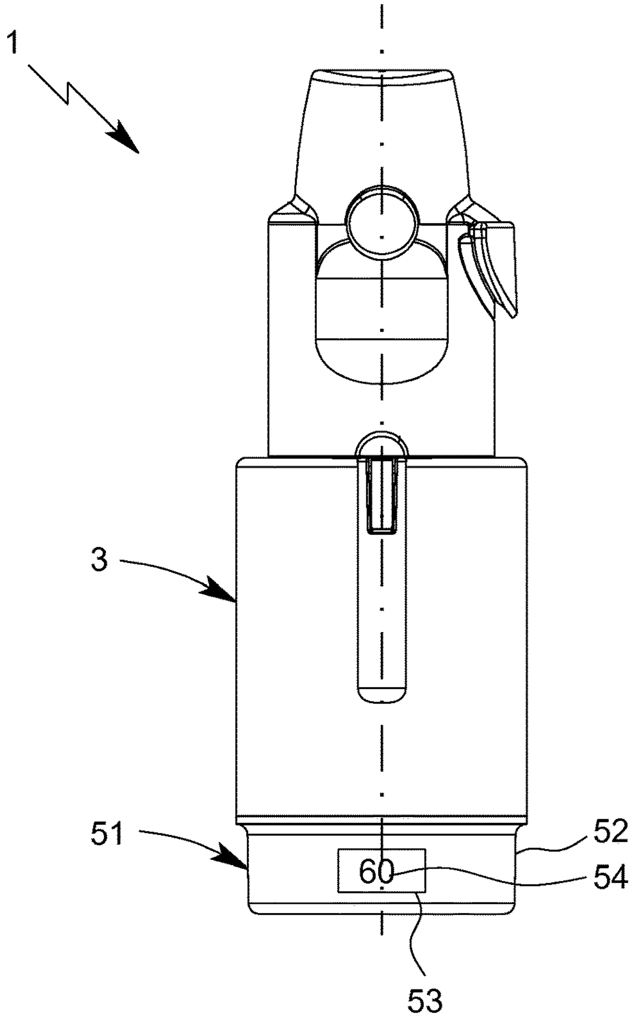
FIG. 10 a side view of the nebulizer according to FIG. 9, rotated by 90°.

The indicator device 51 is preferably arranged at the bottom 29 of the nebulizer 1 or reservoir 3. In particular, the indicator device 51 comprises or forms a first axial end and/or the bottom 29 of the nebulizer 1 or reservoir 3, as best seen in FIGS. 9 and 10.

The indicator device 51 is preferably directly and/or rigidly fixed/attached to the housing part 7 of the reservoir 3.

Preferably, the indicator device 51 and the housing part 7 are connected in a form-fit, snap-fit and/or sealing manner.

Preferably, the indicator device 51 comprises a preferably cylindrical indicator housing 52 and/or has an at least essentially cylindrical form.

The indicator housing 52 preferably comprises a window 53, in particular in the circumferential wall, preferably wherein a relevant marking 54 for indicating the number of uses already performed or still possible with the respective reservoir 3 or bag 4 is visible through the window 53 for a user or patient.

Figure 12:
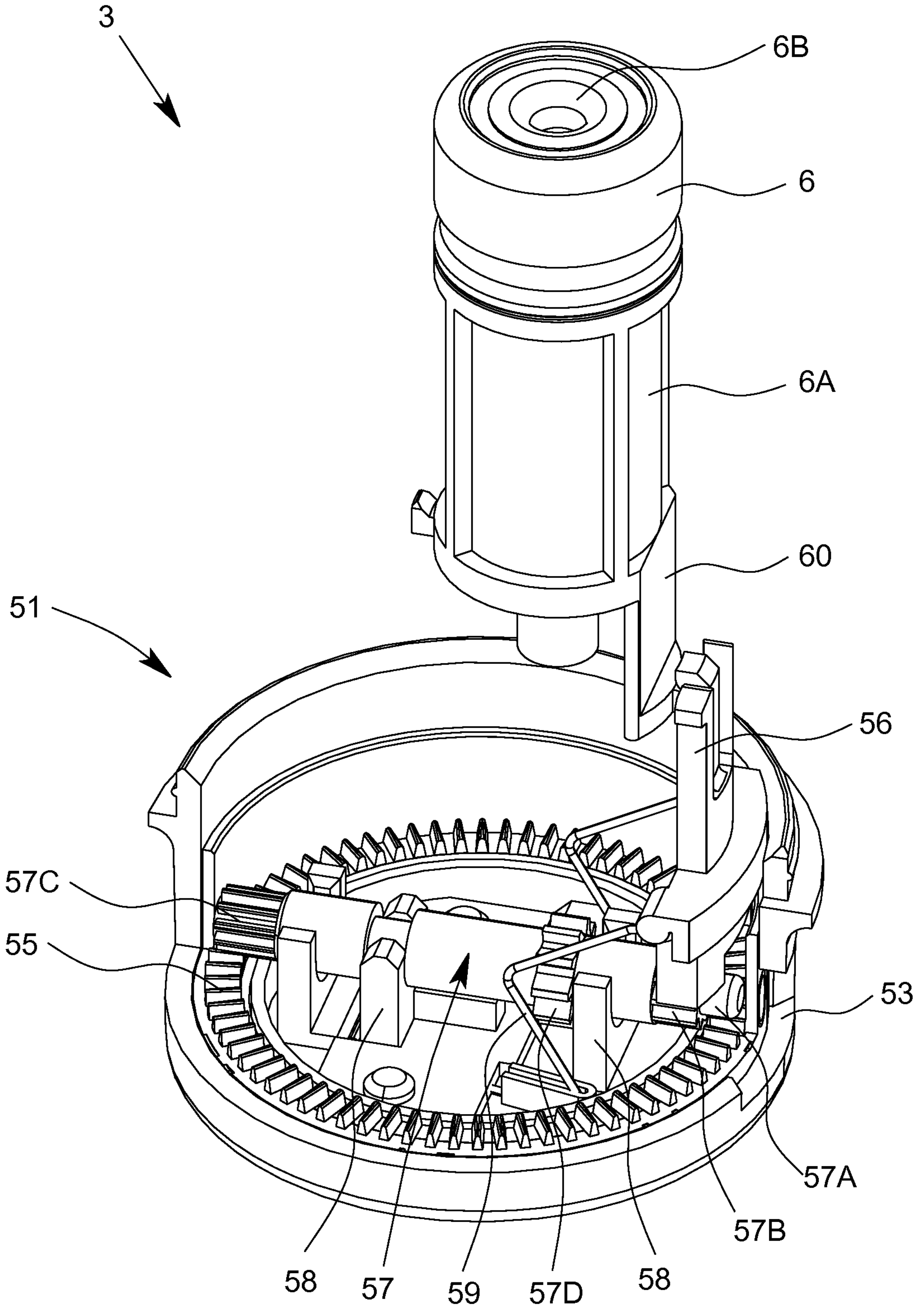
FIG. 12 a schematic section of the nebulizer according to FIG. 9.

FIG. 12 shows a partial section of the reservoir 3 and will be used in the following to describe the functionality of the indicator device 51.

The indicator device 51 preferably comprises an indicator element 55, an associated actuation element 56 and/or a transmission/gear 57 for indexing the indicator element 55 and/or for causing the indexing of the indicator element 55.

The actuation element 56 is preferably adapted to directly or indirectly actuate or index the indicator element 55.

The term “indexing” means preferably that the indicator element 55 is moved forward in increments or steps, in particular for counting and/or indicating the number of uses performed or still possible with the reservoir 3.

Preferred is an indirect actuation or driving so that the actuation element 56 actuates or drives the indicator element 55 via transmission 57.

Preferably, an axial movement of the connector 6, driving part 60 and/or actuation element 56 is transformed into a rotational movement of the indicator element 55, preferably relative to the indicator housing 52, in particular by means of the transmission 57. With other words, the transmission 57 is preferably adapted to transmit the movement of the actuation element 56 to a movement of the indicator element 55.

The transmission 57 preferably comprises a shaft 57A, preferably wherein the shaft 57A, i.e. its rotational axis, is arranged at least essentially perpendicular, to the central axis R of the reservoir 3 and/or extends diagonally through the indicator housing 52.

The transmission 57 preferably comprises a first gear wheel 57B and a second gear wheel 57C, preferably wherein the first gear wheel 57B interacts with the actuation element 56 and/or the second gear wheel 57C interacts with the indicator element 55.

The movement of actuation element 56 causes preferably a rotation of the transmission 57 around its rotation axis, preferably wherein the rotation axis is at least essentially perpendicular to the direction of the movement of the actuation element 56.

The transmission 57 is preferably rotatably held by the indicator housing 52, in particular by at least two bearing sections 58, preferably wherein the bearing sections 58 are located at the bottom of the indicator housing 52. Preferably, the bearing sections 58 comprise recesses for rotatably holding the shafts 57A of the transmission 57.

Optionally, the indicator device 51 comprises a ratchet 57D preventing any counter-rotation of the transmission 57, in particular its shaft 57A. In the present embodiment, the ratchet 57D is formed by an interlock and an arm (not shown) engaging into the interlock.

The indicator housing 52 preferably bears the indicator element 55 such that it can rotate, preferably around the central axis R of the reservoir 3.

The indicator device 51 preferably comprises an actuation spring 59, in particular for biasing the actuation element 56 into a preferred direction, in the drawing upwards, and/or for driving the indicator element 55.

The indicator element 55 is preferably annular and/or embodied as a ring. Preferably, the indicator element 55 is embodied as an annular gear and/or comprises a gearing, preferably wherein the gearing interacts with the second wheel 57C of the transmission 57.

The nebulizer 1 or reservoir 3, in particular the connector 6, preferably comprises a driving part 60 for driving the indicator device 51, in particular the actuation element 56.

Preferably, the driving part 60 is embodied as an arm, that is aligned axially and/or arranged eccentrically within the housing part 7.

Preferably, the driving part 60 is held and/or axially guided by/within the housing part 7. Mostly preferred, the housing part 7, in particular the holding device 21, comprises or forms a preferably eccentrical linear guidance for the connector 6, in particular the driving part 60, preferably wherein the linear guidance is formed by a longitudinal groove in the holding device 21 or housing part 7. Due to the eccentrical arrangement of the reservoir 3 relative to the nebulizer 1, in particular its inner part 17 or housing 18, only a short (radial) distance between the connector 6 and the housing part 7 has to be bridged by the driving part 60 and/or linear guidance.

Preferably, the movement of the connector 6 and, thus, of the driving part 60—preferably during the tensioning—causes an axial movement of the actuating element 56 which in turn causes a rotation of the transmission 57 and/or the indicator element 55, preferably via the transmission 57.

With other words, the movement of the connector 6 within the reservoir 3 and/or relative to the housing part 7 and/or bag 4 is used for actuating or triggering the indicator device 51 and/or for counting.

In the present embodiment, the actuation element 56 and the driving part 60 are preferably embodied as separate parts.

Mostly preferred, the driving part 60 is only temporarily (mechanically) connected to the actuation element 56, in particular at the end of the tensioning process and/or such that only a part of the axial movement of the connector 6 and/or driving part 60 is transferred to the actuation element 56. However, other constructional solutions are also possible, in particular wherein the actuation element 56 and the driving part 60 are formed as one piece.

Preferably, the actuation spring 59 biases the actuation element 56 into a first position. The actuation element 56 is moveable from this first position into a second position for actuation of the indicator device 51, in particular indicator element 55.

In the present embodiment, the actuation element 56 is moveable back and forth between the first and second position for indexing the indicator element 55, in particular for incrementally rotating the transmission 57 in one direction to respectively drive indicator element 55.

As any rotation of the transmission 57 is transformed in a preferably reduced rotation of the indicator element 55, thus every movement of the actuation element 56 from the first to the second position or vice versa results in a movement of the indicator element 55.

In the present embodiment, the actuation element 56 is moveable axially, in particular parallel to the central axis R of the reservoir 3 or central axis N of the nebulizer 1 and/or to the stroke movement of the connector 6.

As already mentioned, the indicator device 51 is preferably arranged at the bottom of the nebulizer 1 or reservoir 3. In particular, the indicator device 51 comprises or forms an axial end and/or the bottom 29 of the nebulizer 1 or reservoir 3.

The connector 6 comprises or forms preferably another axial end and/or the top of the reservoir 3. In particular, the connector 6 and/or its outlet comprises or forms an axial end opposite to the axial end or bottom formed by the indicator device 51.

Thus, due to the construction of the reservoir 3, it is possible to actuate the indicator device 51 from the top of the reservoir 3, preferably by means of the connector 6.

Figure 13:
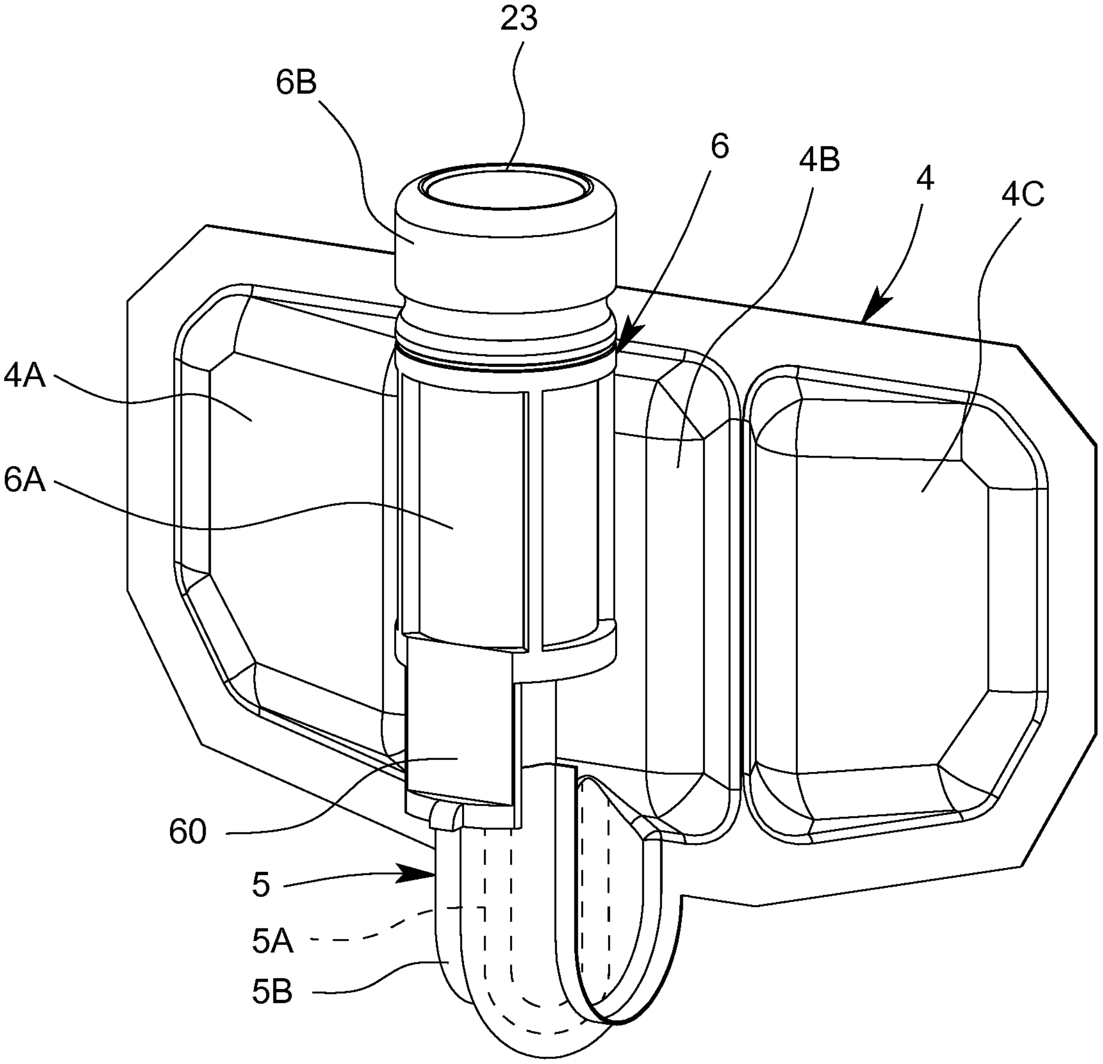
FIG. 13 a perspective view of a preferred embodiment of the bag comprising multiple compartments.
Figure 14:
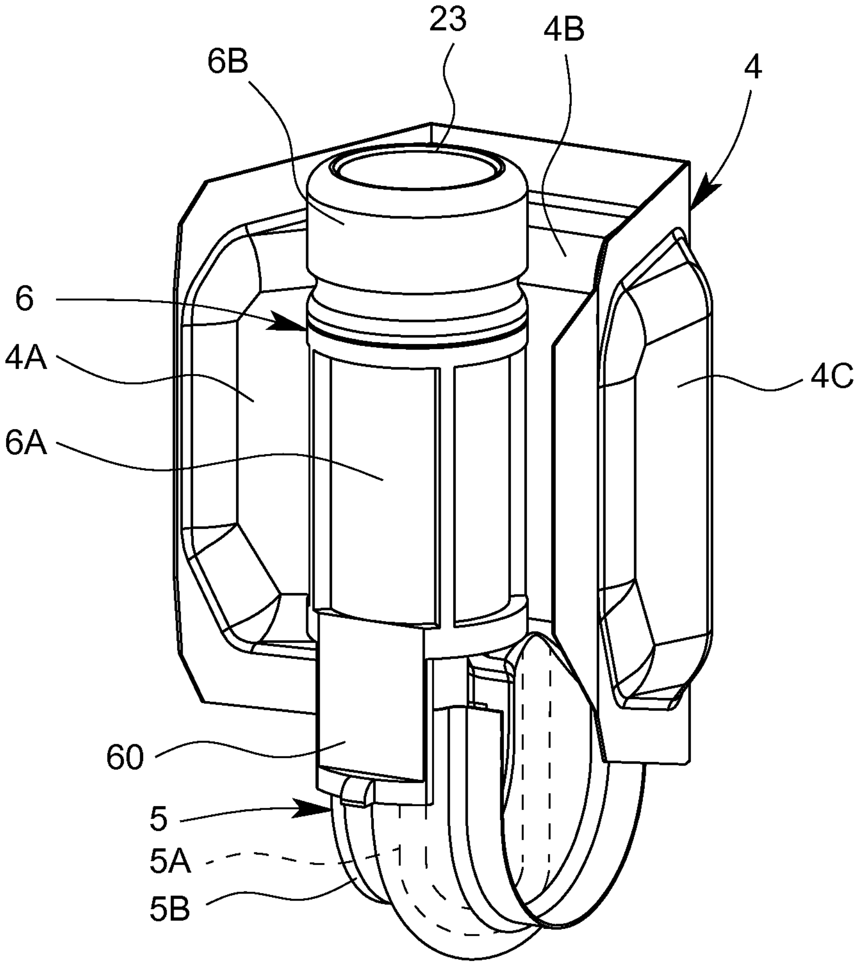
FIG. 14 a perspective view of the bag according to FIG. 13, the compartments being angled towards each other.
Figure 15:
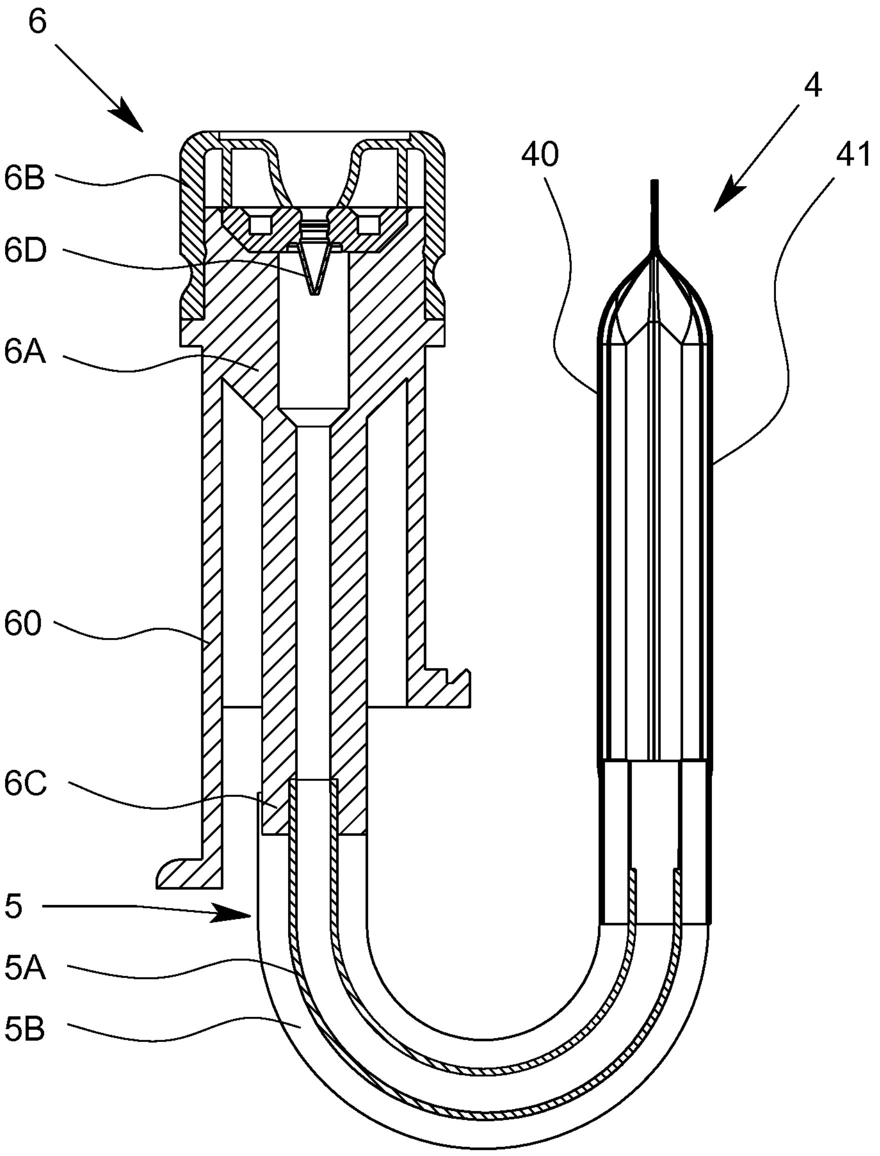
FIG. 15 a schematic section of the bag according to FIG. 13.

FIGS. 13 to 15 show the bag 4, fluid connection 5 and connector 6 according to another preferred embodiment.

As already mentioned, the bag 4 preferably comprises multiple (separate) compartments 4A, 4B, 4C, preferably wherein the compartments 4A-4C are spaced apart from each other, in particular in a circumferential direction of the reservoir 3.

In particular, the compartments 4A-4C are separated from each other by preferably vertical seams, as best seen in FIG. 13.

Preferably, the compartments 4A-4C are fluidically connected to one another. In particular, the fluid connection 5 comprises or forms a joint outlet for the compartments 4A-4C and/or connects fluidically all compartments 4A-4C with the connector 6 and/or conveying element 9 (not shown in FIGS. 13 to 15).

In particular, the compartments 4A-4C are fluidically connected to one another by correspondingly fluid channels.

In the shown embodiment, the fluid connection 5 is fluidically connected with and/or arranged at the center of the bag 4 and/or the compartment 4B that is arranged in the middle of the bag 4. However, other constructional solutions are possible as well.

Preferably, the compartments 4A-4C are or can be angled or bent towards each other, in particular in a U-shaped manner and/or such that the bag 4 at least essentially surrounds the connector 6 and/or the central axis R of the reservoir 3, as best seen in FIG. 14.

In particular, the compartments 4A-4C can be arranged such that each compartment 4A-4C covers or shields the connector 6 on different sides.

Preferably, the bag 4 can be bent/angled/kinked at the seams that separate the compartments 4A-4C from one another.

Preferably, the angle enclosed by two adjacent compartments 4A-4C is of more than 45° or 60°, in particular more than 90° or 120°, and/or less than 180° or 160°, in particular when viewed from the top and/or in direction of the central axis R of the reservoir 3.

In the present embodiment, the bag 4 comprises three compartments 4A-4C, preferably wherein the compartments 4A-4C are angled towards each other by an angle of more than 90° and/or less than 120°. However, other constructional solutions are possible, wherein the bag 4 comprises more than three, in particular four or five, compartments 4A-4C, preferably wherein the compartments 4A-4C are angled towards each other by an angle of more than 120° and/or less than 160°.

In another preferred embodiment (not shown), the reservoir 3 comprises a housing part 7 that is shaped as a prism and/or according to the angular shape of the bag 4.

As already mentioned, the fluid connection 5 preferably comprises a flexible tube 5A, preferably wherein the tube 5A fluidically connects the connector 6 with the bag 4, in particular its compartments 4A-4C.

As best seen in FIG. 15, the fluid connection 5 preferably comprises a cover 5B, in particular wherein the cover 5B covers the tube 5A along its entire length and/or along its entire circumference.

Preferably, the cover 5B is made of the same material as the bag 4. In particular, the cover 5B is formed by laminating the tube 5A into the bag 4 and/or between the sheets 40, 41.

Preferably, an axial end of the tube 5A is inserted into the connector 6.

Preferably, the cover 5B overlaps the axial end of the connector 6. Mostly preferred, an axial end of the connector 6 is laminated into a bag 5 and/or its cover 5B.

In particular, the cover 5B comprises or forms a sealing between the tube 5A and the connector 6 and/or between the tube 5A and/or the bag 4 or its compartments 4A-4C.

In the present embodiment, the connector 6 preferably comprises a connector housing 6A, a port 6B for the conveying element 9, an adapter 6C for the fluid connection 5 and/or a sealing 6D for sealing the fluidical connection between the connector 6 and the conveying element 9.

Figure 16:
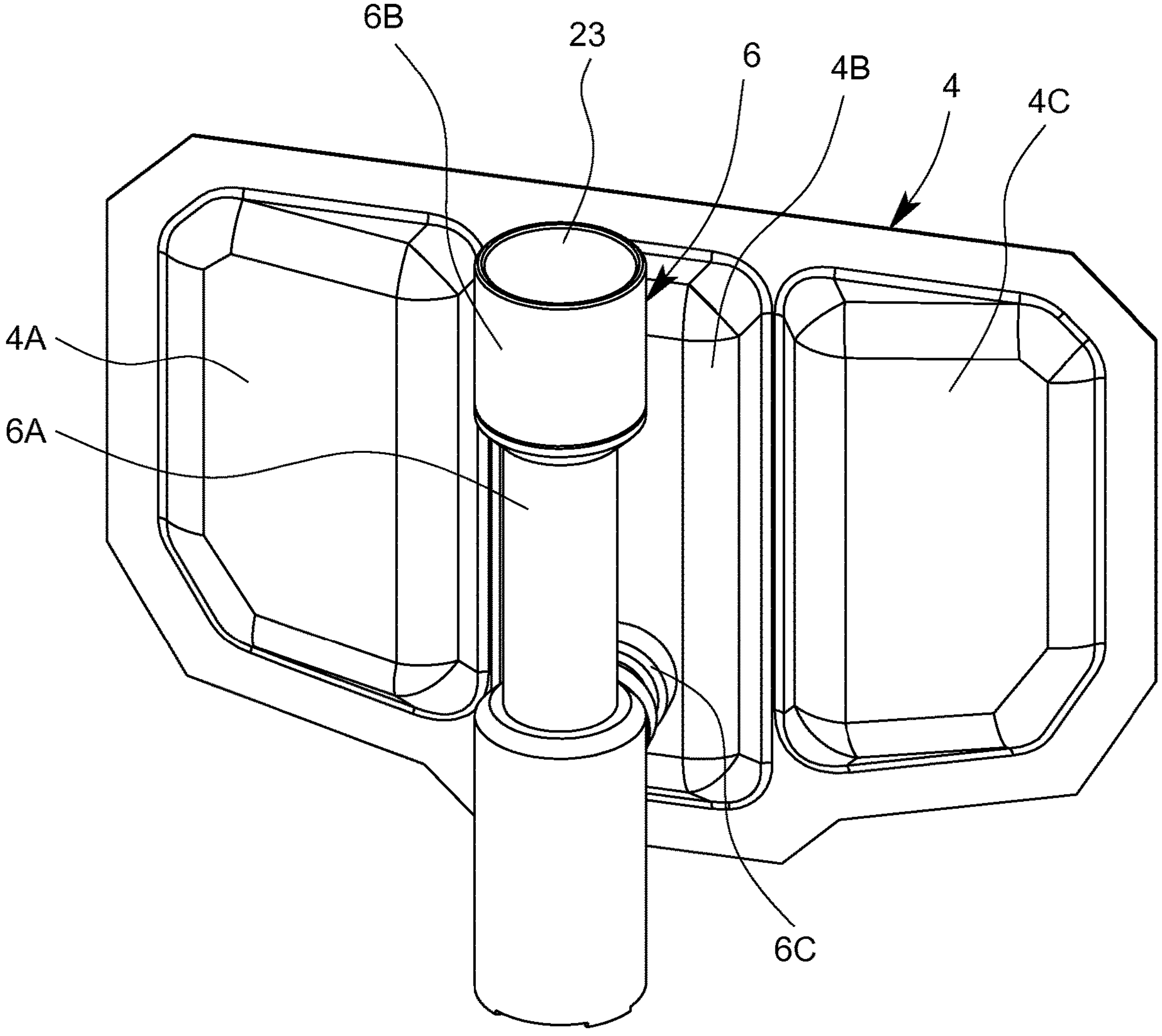
FIG. 16 a perspective view of another embodiment of the bag comprising multiple compartments.
Figure 17:
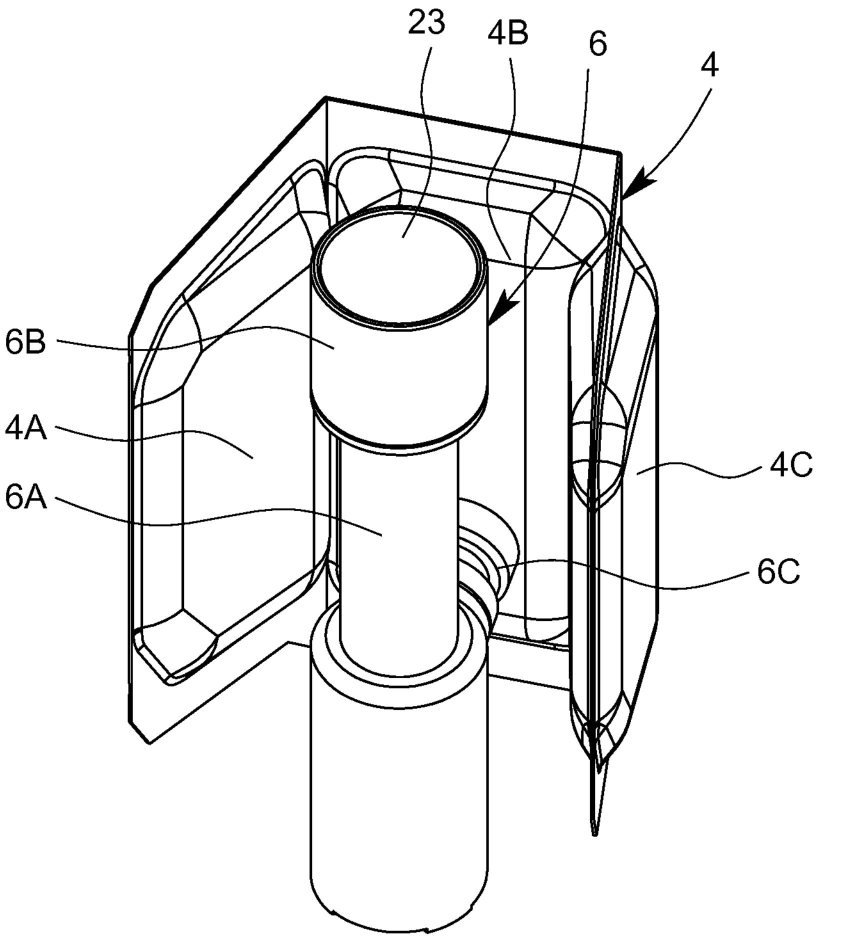
FIG. 17 a perspective view of the bag according to FIG. 16, the compartments being angled towards each other.
Figure 18:
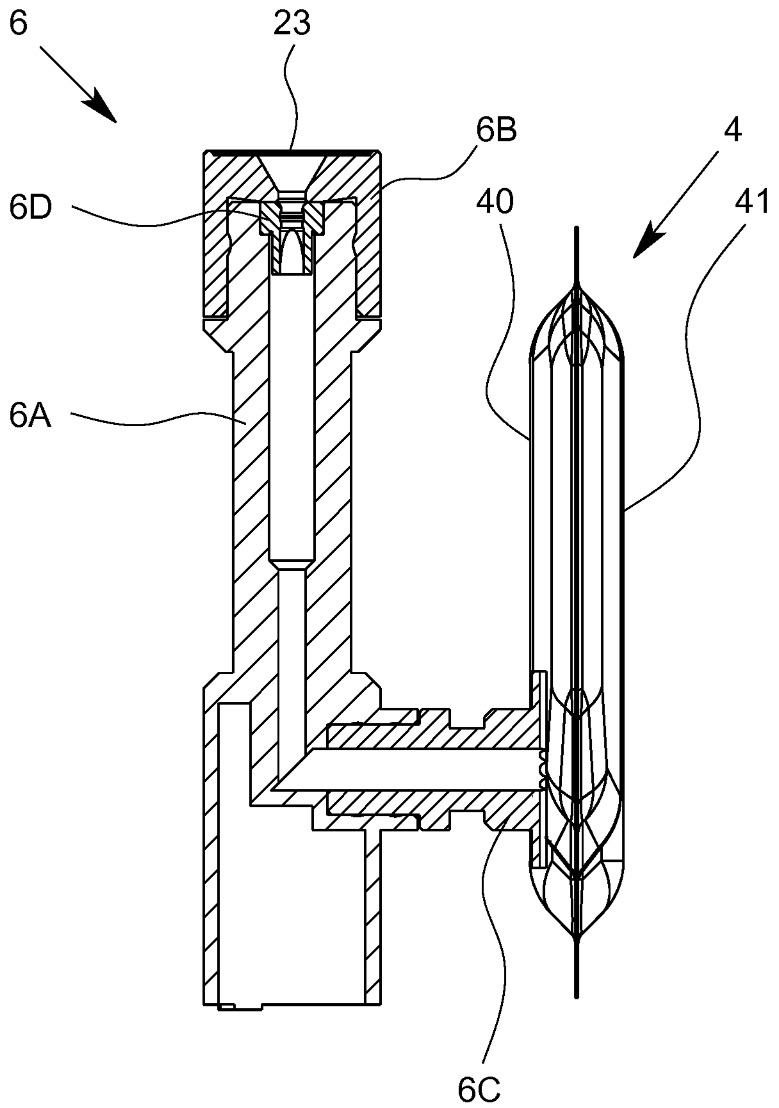
FIG. 18 a schematic section of the bag according to FIG. 17.

FIGS. 16 to 18 show the bag 4, fluid connection 5 and connector 6 according to another embodiment.

In the embodiment shown in FIGS. 16 to 18, the connector 6 is preferably rigidly/immovably connected to the holding device 21 (not shown) and/or housing part 7 (not shown), in particular its bottom.

In particular, the connector 6 is attached to the housing part 7 such that a rotation of the reservoir 3 or housing part 7 relative to the nebulizer 1, in particular its inner part 17 or housing 18, causes a rotation of the connector 6.

In the present embodiment, the connector 6 is preferably embodied as a stand pipe that extends from the bottom 29 to the top of the reservoir 3.

The connector housing 6A is preferably at least essentially cylindrical and/or longitudinal and/or extends from the bottom 29 to the top of the reservoir 3.

Preferably, the connector housing 6A comprises or forms a base of the connector 6 that is rigidly attached to the bottom 29 of the reservoir 3 or housing part 7.

Preferably, the connector housing 6A comprises or forms a fluid channel that extends through the housing part 6A.

The port 6B is preferably adapted to sealingly receive the conveying element 9 (not shown). In particular, the conveying element 9 can be axially guided by the port 6B and/or radially sealed by the sealing 6D, as best seen in FIG. 18.

In the present embodiment, the sealing 6D is preferably embodied as an insert that is inserted into the connector housing 6A and/or port 6B.

Preferably, the port 6B comprises or forms an axial end or top of the connector 6.

The adapter 6C preferably comprises or forms a (rigid) fluid connection between the bag 4 and the connector housing 6A.

In particular, the adapter 6C comprises or forms a fluid channel, preferably wherein the fluid channel extends radially within the housing part 7.

The adapter 6C is at least essentially cylindrical and/or comprises or forms a flange that is attached to and/or inserted into the bag 4 and/or one of its compartments 4A-4C.

In the present embodiment, the connector housing 6A, port 6B, adapter 6C and/or sealing 6D are embodied as separate parts. However, constructional solutions are possible as well, wherein the connector housing 6A, port 6B, adapter 6C and/or sealing 6D are formed integrally and/or as one piece.

As already mentioned, the connector 6 according to the present embodiment is preferably rigidly connected to the housing part 7 and/or immovable relative to the housing part 7 and/or bag 4. Thus, during tensioning and/or actuation of the nebulizer 1, the conveying element 9 and/or holder 14 move(s) relative to the connector 6. This allows a further minimization of the mass which is to be moved together with the reciprocating conveying element 9 and, thus, supports an easy operation and optimized metering or a compact construction.

In the present embodiment, the holder 14 (not shown) might comprise or form the driving part 60 for driving and/or actuating of the indicator device 51, in particular the actuation element 56 thereof.

Individual features, aspects and/or principles of the embodiment described may also be combined with one another as desired and may be used particularly in the shown nebulizer 1, but also in similar or different nebulizers.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers or in other devices for the delivery of liquid formulations.

Preferably, the fluid 2 is a liquid, as already mentioned, especially an aqueous pharmaceutical formulation or an ethanolic pharmaceutical formulation. However, it may also be some other pharmaceutical formulation, a suspension or the like.

Preferred ingredients and/or formulations of the preferably medicinal fluid 2 are listed in particular in WO 2009/115200 A1, preferably on pages 25 to 40, or in EP 2 614 848 A1, paragraphs 0040 to 0087, which are incorporated herewith by reference. In particular, these may be aqueous or non-aqueous solutions, mixtures, formulations containing ethanol or free from any solvent, or the like.

ADDITIONAL EMBODIMENTS

Further, independent aspects of the present invention are listed in the following:

1. Nebulizer (1) for a fluid (2), comprising:

a reservoir (3) containing multiple doses of the fluid (2), and a fluid pump (8) for withdrawing a dose of the fluid (2) from the reservoir (3) and pressurizing the respective dose for nebulization, characterized in that the nebulizer (1) comprises an energy store or drive for driving the fluid pump (8) and/or for nebulization, wherein the reservoir (3) or a tank or bag (4) thereof is arranged around the energy store or drive, and/or that the reservoir (3) or a tank or bag (4) thereof is arranged at least partially around the fluid pump (8) or its pump or pressure chamber (11), and/or that the fluid pump (8) or an associated energy store is actuated or tensioned by manual rotation of the reservoir (3), and/or that the fluid pump (8) comprises a reciprocating conveying element (9), wherein the reservoir (3) is held non-reciprocating by the nebulizer (1) and fluidically connected or connectable via a flexible fluid connection (5) with the conveying element (9), and/or that the reservoir (3) is constructed according to any one of aspects 5 to 33.

2. Nebulizer according to aspect 1, characterized in that the reservoir (3) comprises multiple compartments or bags (4A, 4B) with different fluids (2A, 2B).

3. Nebulizer according to aspect 2, characterized in that the reservoir (3), nebulizer (1) or fluid pump (8) comprises a mixing chamber (36) for mixing the different fluids (2A, 2B), preferably just before nebulization.

4. Nebulizer according to any one of the preceding aspects, characterized in that the reservoir (3) and/or nebulizer (1) comprise a retaining element (19) so that the reservoir (3) can be attached to the nebulizer (1) by force-fit, form-fit and/or snapping.

5. Reservoir (3) for a nebulizer (1), the reservoir (3) comprising:

a tank or bag (4) with multiple doses of a fluid (2) to be nebulized, and a housing part (7), characterized in that the tank or bag (4) is flat and/or extends in an annular and/or circumferential direction within the housing part (7), and/or that the tank or bag (4) is curved in its main extension, and/or that the reservoir (3) comprises a flexible fluid connection (5) and a connector (6) for fluidically connecting the tank or bag (4) to the nebulizer (1).

6. Reservoir according to aspect 5, characterized in that the tank or bag (4) comprises separate compartments with different fluids (2A, 2B).

7. Reservoir according to aspect 5, characterized in that the reservoir (3) comprises multiple tanks or bags (4A, 4B) with different fluids (2A, 2B).

8. Reservoir according to any one of aspects 5 to 7, characterized in that the annular or circumferential extension of the tank(s) or bag(s) (4) is larger than its axial extension or than the axial extension of the housing part (7).

9. Reservoir according to any one of aspects 5 to 8, characterized in that the tank or bag (4) is formed by welded sheet material.

10. Reservoir according to any one of aspects 5 to 9, characterized in that the reservoir (3) comprises a holding device (21) for holding the connector (6) in a defined position in a delivery state of the reservoir (3) or before first use or until the reservoir (3) is connected to the nebulizer (1).

11. Reservoir according to aspect 10, characterized in that the holding device (21) releases the connector (6) and/or allows a reciprocating movement of the connector (6) after the reservoir (3) or connector (6) has been connected to the nebulizer (1).

12. Reservoir according to any one of aspects 5 to 11, characterized in that the flexible fluid connection (5) is formed by or comprises a flexible tube (5A).

13. Reservoir according to any one of aspects 5 to 12, characterized in that the tank or bag (4) is held immovable within the housing part (7) while the connector (6) is moveable in particular in a reciprocating manner in use.

14. Reservoir according to any one of aspects 5 to 13, characterized in that the tank or bag (4) is exchangeable and/or collapsible.

15. Reservoir according to any one of the aspects 5 to 14, characterized in that the reservoir (3) comprises a pump device (39) for—preferably temporarily—pressurizing the fluid (2) to help withdrawing the fluid (2) in doses.

16. Reservoir according to aspect 15, characterized in that the pump device (39) is actuated by reciprocating or stroke-like movement during the tensioning process and/or nebulizing process.

17. Reservoir according to aspects 15 or 16, characterized in that the pump device (39) is embodied as an air pump and/or adapted to pressurize the fluid (2) contained in the tank or bag (4), preferably by pressurizing the air in the housing part (7) and/or a space (28) of the reservoir (3), preferably wherein the space (8) is adapted to receive the tank or bag (4).

18. Reservoir according to any one of the aspects 15 to 17, characterized in that the pump device (39) comprises or forms a piston/cylinder arrangement for pumping air into the reservoir (3), in particular the housing part (7) of the reservoir (3), in order to help withdrawing the fluid (2) in doses from the tank or bag (4) and/or that the connector (6) comprises or forms a piston for the pump device (39) and/or that the housing part (7) comprises or forms a cylinder for the pump device (39).

19. Reservoir according to aspects 15 or 16, characterized in that the pump device (39) is embodied as a bellows and/or comprises a compressible chamber (36) in order to pressurize the fluid (2) contained therein.

20. Reservoir according to any one of the aspects 5 to 19, characterized in that the reservoir (3) comprises a pressurizing device (50), preferably a pressurizing spring, for pressurizing the fluid (2), preferably within the tank or bag (4), in particular constantly and/or independently from tensioning or actuation of the reservoir (3).

21. Reservoir according to aspect 20, characterized in that the pressurizing device (50) presses radially against the tank or bag (4), in particular against a flat side of the tank or bag (4).

22. Reservoir (3) for a nebulizer (1), the reservoir (3) comprising:

a tank or bag (4) with multiple doses of a fluid (2) to be nebulized, and an indicator device (51) for counting or indicating a number of uses performed or still possible with the reservoir (3), characterized in that the indicator device (51) comprises or forms a first axial end and/or a bottom of the reservoir (3) and is actuated/actuatable from a second axial end and/or a top of the reservoir (3), and/or that the reservoir (3) comprises a connector (6) for fluidically connecting the tank or bag (4) with the nebulizer (1), wherein the indicator device (51) is actuated by moving the connector (6) relative to the tank or bag (4), and/or that the reservoir (3) comprises or forms an eccentrical linear guidance for a driving part (60) for driving the indicator device (51), and/or that the reservoir (3) comprises a flexible fluid connection (5) for fluidically connecting the tank or bag (4) to the nebulizer (1), wherein the fluid connection (5) comprises a cover (5B) made of the same material as the tank or bag (4).

23. Reservoir according to aspect 22, characterized in that the reservoir (3) is constructed according to any one of aspects 5 to 21.

24. Reservoir according to aspect 22 or 23, characterized in that the tank or bag (4) comprises more than two compartments, wherein the compartments are angled towards each other, in particular in a U-shaped manner and/or such that the tank or bag (4) at least partially surrounds the connector (6) radially.

25. Reservoir according to any one of the aspects 22 to 24, characterized in that the indicator device (51) is directly and/or rigidly fixed to the housing part (7) of the reservoir (3).

26. Reservoir according to any one of the aspects 22 to 25, characterized in that the indicator device (51) comprises a preferably ring-shaped indicator element (55) and a preferably reciprocatable actuation element (56) for indexing the indicator element (55).

27. Reservoir according to aspect 26, characterized in that the indicator device (51) comprises a transmission (57), wherein the actuation element (56) is mechanically coupled to the indicator element (55) via the transmission (57) and/or wherein a linear movement of the actuation element (56) is transformed to a rotation of the indicator element (55) via the transmission (57).

28. Reservoir according to any one of the aspects 22 to 27, characterized in that the connector (6) comprises or forms a driving part (60) for driving the indicator device (51), in particular for driving the actuation element (56) of the indicator device (51).

29. Reservoir according to any one of the aspects 22 to 28, characterized in that the connector (6) comprises or forms the second axial end and/or the top of the reservoir (3).

30. Reservoir according to any one of the aspects 22 to 29, characterized in that the connector (6) is axially guided and/or circumferentially held in the housing part (7), preferably by means of the linear guidance.

31. Reservoir according to any one of the aspects 22 to 30, characterized in that the connector (6) is arranged eccentrically within the housing part (7) and/or that the longitudinal axis of the connector (6) is radially spaced apart from longitudinal axis of the housing part (7).

32. Reservoir according to any of the aspects 22 to 31, characterized in that the linear guidance is formed by a longitudinal groove in the connector (6) or housing part (7).

33. Reservoir according to any of the aspects 22 to 32, characterized in that the cover (5B) of the fluid connection (5) and the tank or bag (4) are formed integrally.

34. Nebulizer (1) for a fluid (2), comprising:

a reservoir (3) having a tank or bag (4) containing multiple doses of the fluid (2), and a fluid pump (8) for withdrawing a dose of the fluid (2) from the reservoir (3) and for pressurizing the respective dose for nebulization, wherein the fluid pump (8) comprises a conveying element (9) for fluidically connecting the fluid pump (8) with the reservoir (3), wherein the reservoir (3) comprises a connector (6) for fluidically connecting the reservoir (3) to the conveying element (9), and wherein the reservoir (3) comprises an indicator device (51) for counting or indicating a number of uses performed or still possible with the reservoir (3), characterized in that the indicator device (51) comprises or forms an axial end and/or a bottom of the nebulizer (1), and/or that a housing part (7) of the reservoir (3) is attached in a non-reciprocating manner to the fluid pump (8) and that the connector (6) is axially moveable relative to the tank or bag (4) for actuation of the indicator device (51), and/or that the fluid pump (8) comprises a driving part (60) for driving the indicator device (51), wherein the driving part (60) extends next to the connector (6) into the reservoir (3), and/or that the reservoir (3) is constructed according to any one of aspects 5 to 33.

35. Nebulizer according to aspect 34, characterized in that the nebulizer (1) is constructed according to any one of aspects 1 to 4.

36. Nebulizer according to aspects 34 or 35, characterized in that the nebulizer (1) comprises a holder (14) for mechanically connecting fluid pump (8) with the connector (6), wherein the holder (14) is rotatable and/or axially reciprocatable together with the connector (6).

LIST OF REFERENCE NUMERALS

1 nebulizer
2 fluid
3 reservoir
4 bag
4A bag/compartment
4B bag/compartment
4C bag/compartment
5 fluid connection
5A tube
5B cover
6 connector
6A connector housing
6B port
6C adapter
6D sealing
7 housing part
8 fluid pump
9 conveying element
10 non-return valve
11 pressure chamber
12 nozzle
13 mouthpiece
14 holder
15 drive spring
16 blocking element
17 inner part
18 housing
19 retaining element
20 septum
21 holding device
22 biasing device
23 cover
24 receptacle
25 central portion
26 inner portion
27 end portion
28 space
29 bottom
30 stop
31 engagement element
32 recess
33 head
34 shaft

35 end
36 mixing chamber
37 filter
38 holding element
39 pump device
39A sealing element
39B groove
39C air leakage
40 sheet
41 sheet
42 longitudinal seam
43 transversal seam
44 inlet
45 outlet
46 intermediate seam
47 connecting element
48 valve
49 opening
50 pressurizing device
51 indicator device
52 indicator housing
53 window
54 marking
55 indicator element
56 actuation element
57 transmission/gear
57A shaft
57B first gear wheel
57C second gear wheel
57D ratchet
58 bearing section
59 actuation spring
60 driving part
A aerosol
R axis of reservoir
N axis of nebulizer
S separation line

The invention claimed is:

1. A reservoir (3) for a nebulizer (1), the reservoir (3) comprising:

a collapsible bag (4) with multiple doses of a fluid (2) to be nebulized, and a housing part (7) containing the collapsible bag (4), wherein the collapsible bag (4) extends in a circumferential direction within the housing part (7) and/or is curved around a central axis (R) of the reservoir (3), and/or wherein the reservoir (3) comprises a flexible fluid connection (5) and a connector (6) for fluidically connecting the collapsible bag (4) to the nebulizer (1).

2. The reservoir according to claim 1, wherein at least one of:

the collapsible bag (4) comprises multiple compartments (4A, 4B, 4C), and the compartments (4A, 4B, 4C) are at least essentially flat.

3. The reservoir according to claim 2, wherein at least one of:

the compartments (4A, 4B, 4C) are angled towards each other, the compartments (4A, 4B, 4C) are angled towards each other in a U-shaped manner and the compartments (4A, 4B, 4C) are angled towards each other such that the collapsible bag (4) at least partially surrounds at least one of the connector (6) and the central axis (R) of the reservoir (3).

4. The reservoir according to claim 2, wherein at least one of:

the compartments (4A, 4B, 4C) are fluidically connected to one another, and the fluid connection (5) comprises or forms a joint outlet for the compartments (4A, 4B, 4C).

5. The reservoir according to claim 1, wherein the reservoir (3) comprises multiple tanks or bags (4).

6. The reservoir according to claim 2, wherein at least one of:

the reservoir (3) comprises different fluids (2A, 2B, 2C), each fluid (2) is contained in different compartments (4A, 4B, 4C), and each fluid (2) is contained in different collapsible bags (4).

7. The reservoir according to claim 6, wherein at least one of:

the reservoir (3) comprises a mixing chamber (36) for mixing the different fluids (2A, 2B, 2C), and the mixing chamber (36) mixes the different fluids (2A, 2B, 2C) just before nebulization.

8. The reservoir according to claim 1, wherein at least one of:

the collapsible bag (4) is at least essentially flat, and an annular/circumferential extension of the collapsible bag (4) is larger than at least one of an axial extension of the collapsible bag (4), and an axial extension of the housing part (7).

9. The reservoir according to claim 1, wherein at least one of:

the collapsible bag (4) is formed by a sheet (40, 41)

the collapsible bag (4) is formed by a welded sheet (40, 41), and the collapsible bag (4) is made of plastics.

10. The reservoir according to claim 1, wherein the collapsible bag (4) is exchangeable.

11. The reservoir according to claim 1, wherein at least one of:

the reservoir (3) comprises or forms a holding device (21) for at least one of holding and guiding the connector (6), the housing part (7) comprises or forms a holding device (21) for at least one of holding and guiding the connector (6), and the holding device of at least one of the reservoir (3) and the housing part (7) at least one of circumferentially, radially, and axially at least one of holds and guides the connector (6).

12. The reservoir according to claim 11, wherein at least one of:

the holding device (21) holds the connector (6) in a delivery state of the reservoir (3) or before first use or until the reservoir (3) is connected to the nebulizer (1), and the holding device (21) releases the connector (6) and/or allows a reciprocating movement of the connector (6) after the reservoir (3) or connector (6) has been connected to the nebulizer (1).

13. The reservoir according to claim 1, wherein the flexible fluid connection (5) is formed by, or comprises, a flexible tube (5A).

14. The reservoir according to claim 1, wherein at least one of:

the fluid connection (5) is at least partially laminated into the collapsible bag (4), a flexible tube (5A) of the fluid connection (5) is at least partially laminated into the collapsible bag (4), and an axial end of the flexible tube (5A) of the fluid connection (5) is at least partially laminated into the collapsible bag (4).

15. The reservoir according to claim 1, wherein at least one of:

the fluid connection (5) comprises a cover (5B), and the cover (5B) is made of aluminium, and the cover (5B) is made of a same material as the collapsible bag (4).

16. The reservoir according to claim 15, wherein the cover (5B) of the fluid connection (5) and the collapsible bag (4) are formed integrally.

17. The reservoir according to claim 1, wherein at least one of:

the collapsible bag (4) is immovable relative to the housing part (7), the connector (6) is moveable in a reciprocating manner, relative to at least one of the collapsible bag (4) and the housing part (7), the connector (6) is axially moveable relative to at least one of the collapsible bag (4) and the housing part (7), and the connector (6) is axially moveable in a reciprocating manner relative to at least one of the collapsible bag (4) and the housing part (7).

18. The reservoir according to claim 1, wherein at least one of:

the reservoir (3) comprises a pump device (39) for pressurizing the fluid (2) to help withdrawing the fluid (2) in doses, and the pump device (39) temporarily pressurizes the fluid (2) to help withdrawing the fluid (2) in doses.

19. The reservoir according to claim 18, wherein at least one of:

the pump device (39) is embodied as an air pump, the pump device (39) is adapted to pressurize the fluid (2) contained in the collapsible bag (4), and the pump device (39) is adapted to pressurize the fluid (2) contained in the collapsible bag (4) by pressurizing the air in at least one of the housing part (7) and a space (28) of the reservoir (3) containing the collapsible bag (4).

20. The reservoir according to claim 18, wherein at least one of:

the pump device (39) comprises or forms a piston/cylinder arrangement, the piston/cylinder arrangement helps in withdrawing the fluid (2) in doses from the collapsible bag (4), the connector (6) comprises or forms a piston of the pump device (39), and the housing part (7) comprises or forms a cylinder of the pump device (39).

21. The reservoir according to claim 18, wherein at least one of:

the pump device (39) is embodied as a bellows in order to pressurize the fluid (2) contained therein, and the pump device (39) comprises a compressible chamber (36) in order to pressurize the fluid (2) contained therein.

22. The reservoir according to claim 1, wherein at least one of:

the reservoir (3) comprises a pressurizing device (50) for pressurizing the fluid (2), the pressurizing device (50) pressurizes the fluid (2) within the collapsible bag (4), the pressurizing device (50) includes a pressurizing spring for pressurizing the fluid (2), and the pressurizing device (50) pressurizes the fluid (2) constantly and/or independently from a movement of the connector (6).

23. The reservoir according to claim 22, wherein at least one of:

the pressurizing device (50) presses radially against the collapsible bag (4), and the pressurizing device (50) presses radially against a flat side of the collapsible bag (4).

24. The reservoir according to claim 1, wherein the reservoir (3) comprises an indicator device (51) for counting or indicating a number of uses performed or still possible with the reservoir (3).

25. The reservoir according to claim 24, wherein the indicator device (51) comprises or forms a first axial end and/or a bottom (29) of the reservoir (3) and/or that the indicator device (51) is actuated/actuatable from a second axial end and/or a top of the reservoir (3).

26. The reservoir according to claim 24, wherein the connector (6) comprises or forms the second axial end and/or the top of the reservoir (3).

27. The reservoir according to claim 24, wherein the indicator device (51) is actuated by moving the connector (6) relative to the collapsible bag (4).

28. The reservoir according to claim 24, wherein the indicator device (51) is directly and/or rigidly fixed to the housing part (7) of the reservoir (3).

29. The reservoir according to claim 24, wherein at least one of:

the indicator device (51) comprises an indicator element (55) for indexing the indicator element (55), the indicator element (55) is ring-shaped, and the indicator device (51) comprises a reciprocatable actuation element (56) for indexing the indicator element (55).

30. The reservoir according to claim 29, wherein at least one of:

the indicator device (51) comprises a transmission (57), the actuation element (56) is mechanically coupled to the indicator element (55) via the transmission (57), and a linear movement of the actuation element (56) is transformed to a rotation of the indicator element (55) via the transmission (57).

31. The reservoir according to claim 24, wherein at least one of:

the connector (6) comprises or forms a driving part (60) for driving the indicator device (51), and the driving part (60) operates to drive the actuation element (56) of the indicator device (51).

32. The reservoir according to claim 31, wherein at least one of:

the reservoir (3) comprises or forms guidance for the connector (6), the holding device (21) comprises or forms guidance for the connector (6), the guidance is eccentrical linear, and the guidance operates on the driving part (60).

33. The reservoir according to claim 32, wherein at least one of:

the linear guidance is formed by a longitudinal groove in the housing part (7), and the longitudinal groove is in the holding device (21) of the housing part (7).

34. The reservoir according to claim 1, wherein at least one of:

the connector (6) is eccentrically arranged and/or guided within at least one of the reservoir (3), and the housing part (7), and the central axis of the connector (6) is radially spaced apart from central axis (R) of at least one of the reservoir (3), and the housing part (7).

35. A nebulizer (1) for a fluid (2), comprising:

a reservoir (3) containing multiple doses of the fluid (2), and a fluid pump (8) for withdrawing a dose of the fluid (2) from the reservoir (3) and pressurizing the respective dose for nebulization, wherein the reservoir (3) comprises:

a tank or bag (4) with multiple doses of a fluid (2) to be nebulized, and a housing part (7) containing the tank or bag (4), wherein the tank or bag (4) extends in a circumferential direction within the housing part (7) and/or is curved around a central axis (R) of the reservoir (3), and/or wherein the reservoir (3) comprises a flexible fluid connection (5) and a connector (6) for fluidically connecting the tank or bag (4) to the nebulizer (1).

36. A nebulizer (1) for a fluid (2), comprising:

a reservoir (3) containing multiple doses of the fluid (2), wherein the reservoir (3) comprises:

a tank or bag (4) with multiple doses of a fluid (2) to be nebulized, and a housing part (7) containing the tank or bag (4), wherein the tank or bag (4) extends in a circumferential direction within the housing part (7) and/or is curved around a central axis (R) of the reservoir (3), and/or wherein the reservoir (3) comprises a flexible fluid connection (5) and a connector (6) for fluidically connecting the tank or bag (4) to the nebulizer (1); and a fluid pump (8) for withdrawing a dose of the fluid (2) from the reservoir (3) and pressurizing the respective dose for nebulization, wherein the reservoir (3) or a tank or bag (4) thereof is arranged at least partially around an energy store or drive of the nebulizer (1) for driving the fluid pump (8) and/or at least partially around the fluid pump (8) or its pump or pressure chamber (11).

37. The nebulizer according to claim 36, wherein at least one of:

the fluid pump (8) comprises a reciprocating conveying element (9), at least one of the reservoir (3) and the tank or bag (4), is held non-reciprocating by the nebulizer (1) and is fluidically connected or connectable via a fluid connection (5) with the conveying element (9), and the fluid connection (5) is flexible.

38. The nebulizer according to claim 36, wherein the tank or bag (4) comprises multiple compartments (4A, 4B, 4C).

39. The nebulizer according to claim 38, wherein the compartments (4A, 4B, 4C) are angled towards each other.

40. The nebulizer according to claim 36, wherein at least one of:

at least one of the tank or bag (4) and the compartments (4A, 4B, 4C), is/are arranged in a U-shaped manner around at least one of the fluid pump (8), the pump or pressure chamber (11), and the energy store or drive of the nebulizer (1), and at least one of the tank or bag (4) and the compartments (4A, 4B, 4C), is/are arranged such that the tank or bag (4) at least partially surrounds the central axis (R) of the reservoir (3) and/or fluid pump (8).

41. The nebulizer according to claim 36, wherein at least one of:

the central axis (R) of the reservoir (3) is spaced apart from the central axis (N) of at least one of the nebulizer (1) and the fluid pump (8), and at least one of the fluid pump (8) and the energy store or drive is arranged eccentrically within the reservoir (3).

42. A nebulizer (1) for a fluid (2), comprising:

a reservoir (3) containing multiple doses of the fluid (2), wherein the reservoir (3) comprises:

a collapsible bag (4) with multiple doses of a fluid (2) to be nebulized, and a housing part (7) containing the collapsible bag (4), wherein the collapsible bag (4) extends in a circumferential direction within the housing part (7) and/or is curved around a central axis (R) of the reservoir (3), and/or that the reservoir (3) comprises a flexible fluid connection (5) and a connector (6) for fluidically connecting the collapsible bag (4) to the nebulizer (1); and a fluid pump (8) for withdrawing a dose of the fluid (2) from the reservoir (3) and pressurizing the respective dose for nebulization, characterized in that the fluid pump (8) comprises a reciprocating conveying element (9), wherein the reservoir (3) is held non-reciprocating by the nebulizer (1) and fluidically connected or connectable via a preferably flexible fluid connection (5) with the conveying element (9).

43. The nebulizer according to claim 42, wherein the reservoir (3) or the collapsible bag (4) thereof is arranged at least partially around a central axis (N) of the nebulizer (1), around the fluid pump (8) or its pump or pressure chamber (11) and/or around an energy store or drive of the nebulizer (1) for driving the fluid pump (8).

44. The nebulizer according to claim 42 wherein at least one of:

the reservoir (3) comprises the collapsible bag (4) containing the fluid (2), a connector (6) for fluidically connecting the collapsible bag (4) to the conveying element (9) and a housing part (7) containing the collapsible bag (4), and the connector (6) is axially moveable relative to at least one of the collapsible bag (4) the housing part (7), and the conveying element (9).

45. The nebulizer according to claim 44, wherein at least one of:

the housing part (7) is attached in a non-reciprocating manner to at least one of the nebulizer (1) and an inner part (17) of the nebulizer (1), and the connector (6) is held in a reciprocating manner by at least one of the nebulizer (1) and a holder (14) of the nebulizer (1).

46. The nebulizer according to claim 44, wherein at least one of:

the nebulizer (1) comprises a holder (14) for mechanically holding the connector (6), and the holder (14) is rotatable and/or axially moveable together with the connector (6) and/or the conveying element (9).

47. The nebulizer according to claim 35, wherein the reservoir (3) comprises an indicator device (51) for counting or indicating a number of uses performed or still possible with the reservoir (3).

48. The nebulizer according to claim 47, wherein indicator device (51) comprises or forms an axial end and/or a bottom (29) of the nebulizer (1) or reservoir (3).

49. The nebulizer according to claim 47, wherein at least one of:

the nebulizer (1) comprises a driving part (60) for driving the indicator device (51), the driving part (60) is axially moveable, and the driving part (60) is axially moveable together with the conveying element (9).

50. The nebulizer according to claim 49, wherein the connector (6) or the holder (14) of the nebulizer (1) comprises or forms the driving part (60).

51. The nebulizer according to claim 35, wherein the reservoir (3) comprises multiple compartments or bags (4A, 4B, 4C) with different fluids (2A, 2B).

52. The nebulizer according to claim 35, wherein at least one of:

the reservoir (3), nebulizer (1) or fluid pump (8) comprises a mixing chamber (36) for mixing different fluids (2A, 2B, 2C), and the mixing chamber (36) mixes the different fluids (2A, 2B, 2C) just before nebulization.

53. The nebulizer according to claim 35, wherein at least one of:

at least one of the reservoir (3) the housing part (7), the nebulizer (1), and an inner part (18) of the nebulizer (1), includes a retaining element (19) so that the reservoir (3) is attached to the nebulizer (1) by force-fit, form-fit and/or snapping.

* * * * *